(12) United States Patent
Kambe et al.

(10) Patent No.: US 10,252,963 B2
(45) Date of Patent: Apr. 9, 2019

(54) METHOD FOR PRODUCING METHANOL AND APPARATUS FOR PRODUCING METHANOL

(71) Applicant: MITSUBISHI GAS CHEMICAL COMPANY, INC., Tokyo (JP)

(72) Inventors: Yasuaki Kambe, Niigata (JP); Kohei Uchida, Niigata (JP); Hiroshi Watanabe, Niigata (JP); Daigo Hirakawa, Niigata (JP); Tatsuya Hasegawa, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/519,003

(22) PCT Filed: Oct. 20, 2015

(86) PCT No.: PCT/JP2015/079580
§ 371 (c)(1),
(2) Date: Apr. 13, 2017

(87) PCT Pub. No.: WO2016/063872
PCT Pub. Date: Apr. 28, 2016

(65) Prior Publication Data
US 2017/0240492 A1 Aug. 24, 2017

(30) Foreign Application Priority Data
Oct. 20, 2014 (JP) .................................. 2014-214081

(51) Int. Cl.
*C07C 29/152* (2006.01)
*C07C 31/04* (2006.01)
(Continued)

(52) U.S. Cl.
CPC ............ *C07C 29/152* (2013.01); *B01J 8/0492* (2013.01); *B01J 8/0496* (2013.01); *B01J 23/80* (2013.01);
(Continued)

(58) Field of Classification Search
CPC ...... C07C 29/152; C07C 31/04; B01J 8/0492; B01J 8/0496; B01J 37/03; B01J 23/80; B01J 37/00; B01J 2208/00106; B01J 2208/00893
See application file for complete search history.

(56) References Cited

U.S. PATENT DOCUMENTS 3,974,735 A 8/1976 Berner
5,767,039 A 6/1998 Yamagishi et al.
(Continued)

FOREIGN PATENT DOCUMENTS

EP 2 492 008 8/2012
EP 02492008 A1 8/2012
(Continued)

OTHER PUBLICATIONS

Li, "Development of highly stable catalyst for methanol synthesis from carbon dioxide", Applied Catalysis A: General, 469; 2014; pp. 306-311.
(Continued)

*Primary Examiner* — Jafar F Parsa
(74) *Attorney, Agent, or Firm* — Greenblum & Bernstein, P.L.C.

(57) ABSTRACT

Synthesizing methanol from a synthesis gas and separating an unreacted gas from a reaction mixture obtained by passing through the synthesis step, the method including a synthesis loop having at least two synthesis steps and at least two separation steps; obtaining a first mixed gas by increasing through a circulator a pressure of a residual gas, obtained by removing a purge gas from the final unreacted gas separated from the final reaction mixture subsequent to the (Continued)

final synthesis step, and by mixing the residual gas with a fraction of a make-up gas; synthesizing methanol; separating a first unreacted gas from the first reaction mixture obtained in the synthesizing step; obtaining a second mixed gas by mixing the first unreacted gas and a fraction of the make-up gas; finally synthesizing methanol; and separating the final unreacted gas from the final reaction mixture obtained in the final synthesis step.

14 Claims, 7 Drawing Sheets

(51) Int. Cl.
    *C07B 61/00*     (2006.01)
    *B01J 8/04*     (2006.01)
    *B01J 23/80*     (2006.01)
    *B01J 37/00*     (2006.01)
    *B01J 37/03*     (2006.01)

(52) U.S. Cl.
    CPC ............... *B01J 37/00* (2013.01); *B01J 37/03* (2013.01); *C07C 31/04* (2013.01); *B01J 2208/00106* (2013.01); *B01J 2208/00893* (2013.01); *C07B 61/00* (2013.01); *Y02P 20/52* (2015.11)

(56) References Cited

U.S. PATENT DOCUMENTS

| | | | |
|---|---|---|---|
| 6,387,963 | B1 | 5/2002 | Fitzpatrick |
| 6,433,029 | B1 | 8/2002 | Fitzpatrick |
| 2005/0197412 | A1* | 9/2005 | Van Egmond ............ C07C 1/20 518/726 |
| 2007/0225385 | A1 | 9/2007 | Early |
| 2007/0293590 | A1* | 12/2007 | Hipp ...................... B01J 8/0496 518/713 |
| 2015/0175509 | A1 | 6/2015 | Almqvist et al. |

FOREIGN PATENT DOCUMENTS

| | | |
|---|---|---|
| JP | 51-10210 | 4/1976 |
| JP | 51-44715 | 11/1976 |
| JP | 06-35401 | 5/1994 |
| JP | 08-299796 | 11/1996 |
| JP | 2695663 | 9/1997 |
| JP | 10-272361 | 10/1998 |
| JP | 2001-205089 | 7/2001 |
| JP | 2002-515467 | 5/2002 |
| JP | 4362013 | 11/2009 |
| WO | 99/59944 | 11/1999 |
| WO | 1999/59945 | 11/1999 |
| WO | 2006/018610 | 2/2006 |
| WO | 2011/048976 | 4/2011 |
| WO | 2014/012601 | 1/2014 |

OTHER PUBLICATIONS

Kuwa et al., "Advanced Utilization Technology of Natural Gas—Frontier of Development Researches", N.T.S., Methanol Synthesis, Chapter 5, Section 2; 2001; pp. 439, 446-447.

International Search Report issued in Patent Application No. PCT/JP2015/079580, dated Jan. 19, 2016.

International Preliminary Report on Patentability issued in PCT/JP2015/079580, dated Apr. 25, 2017.

* cited by examiner

[FIG. 1]
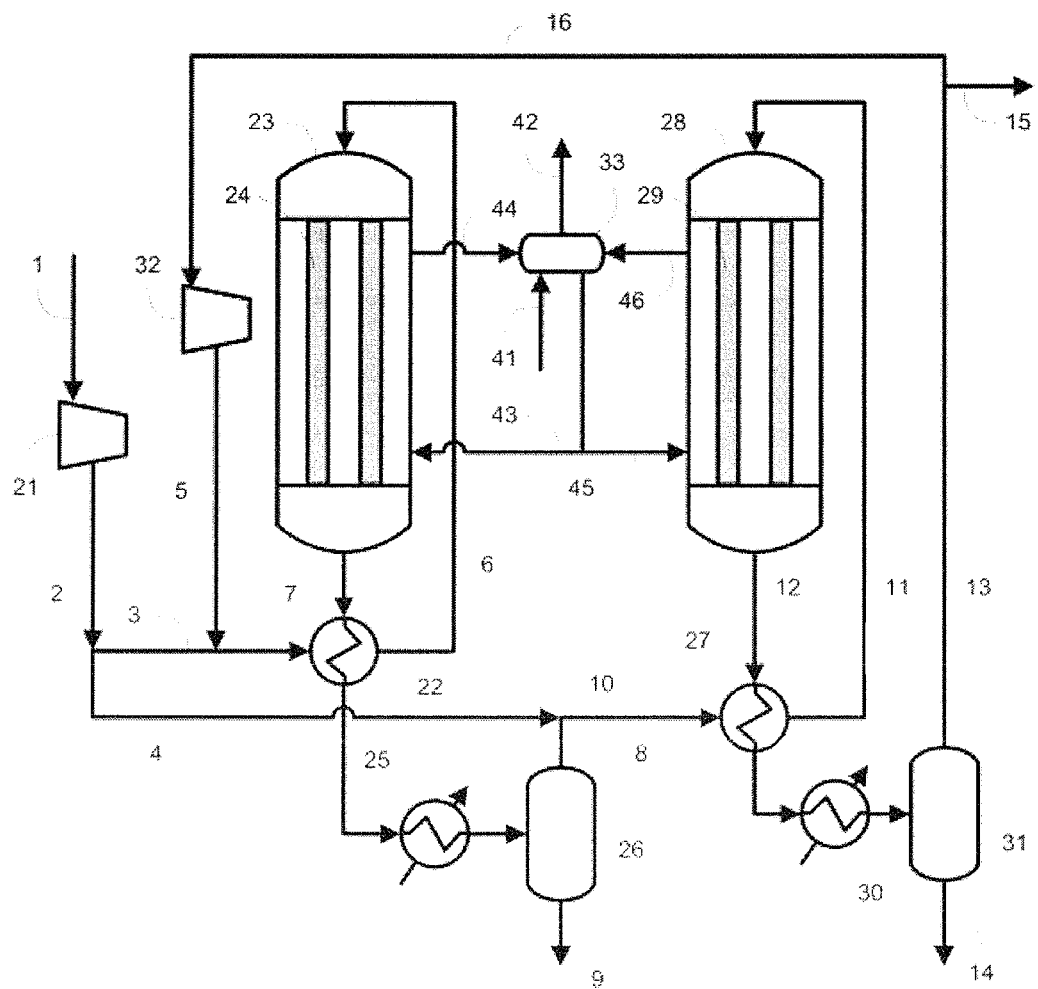

[FIG. 2]
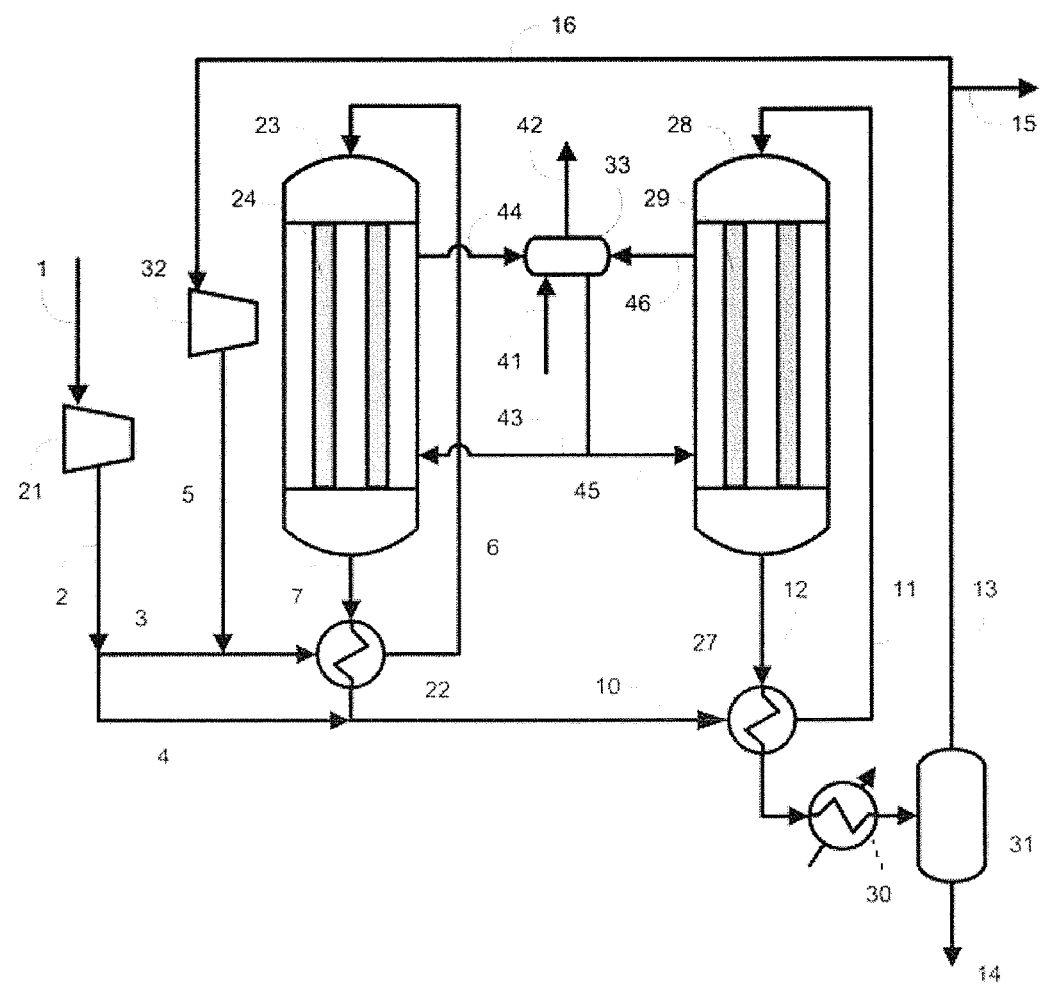

[FIG. 3]
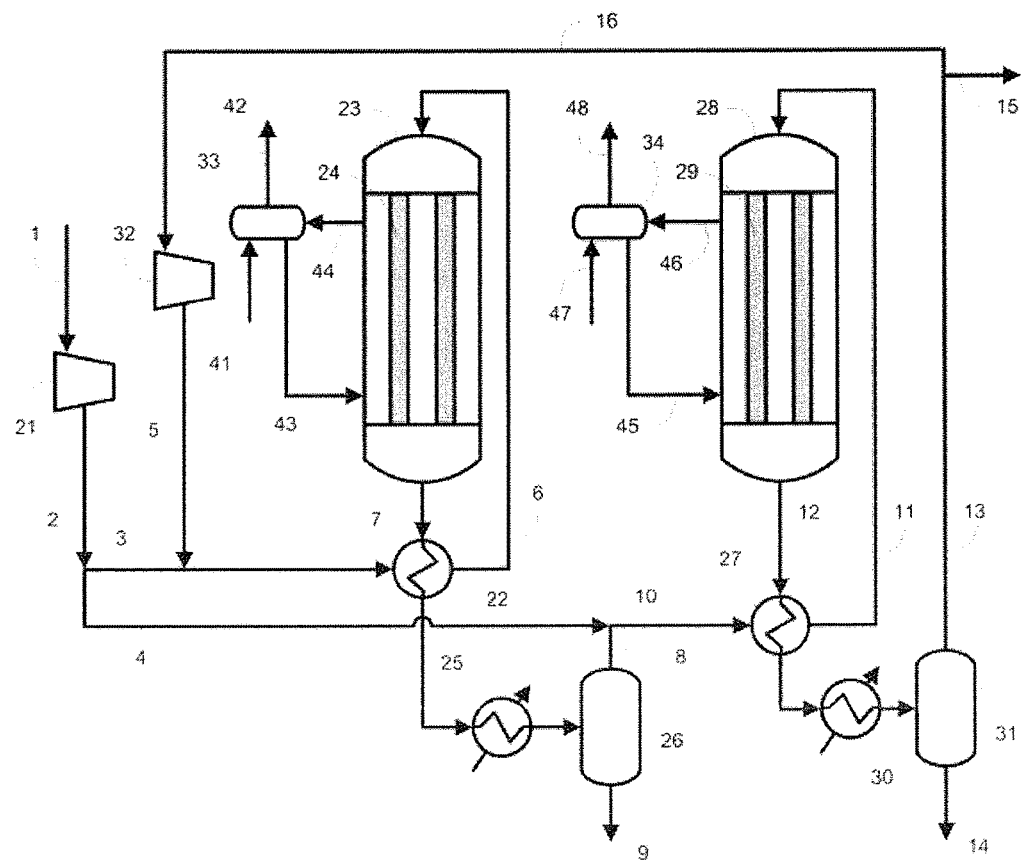

[FIG. 4]
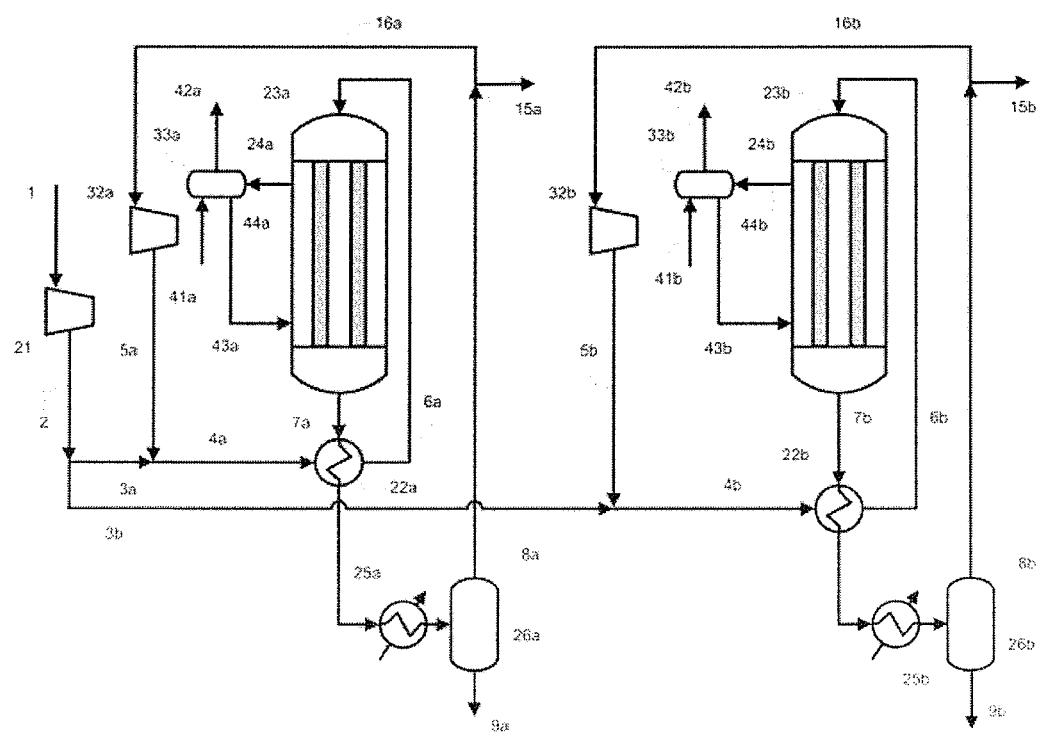

[FIG. 5]
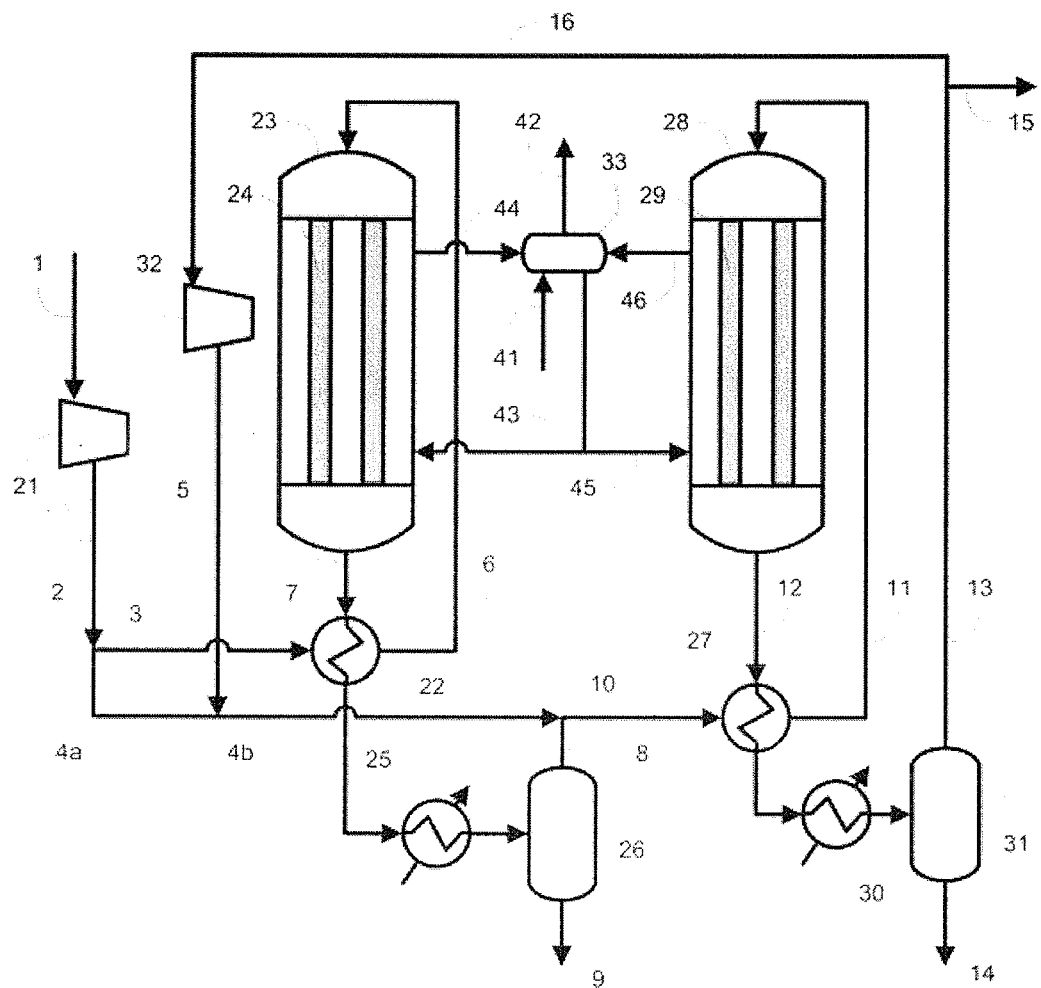

[FIG. 6]
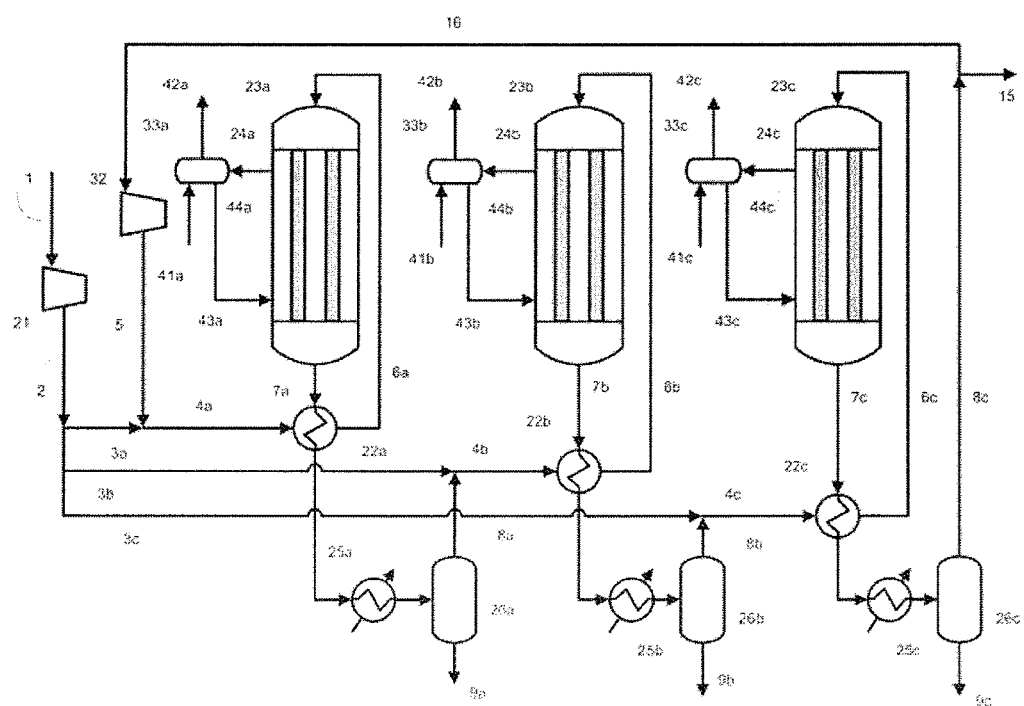

[FIG. 7]
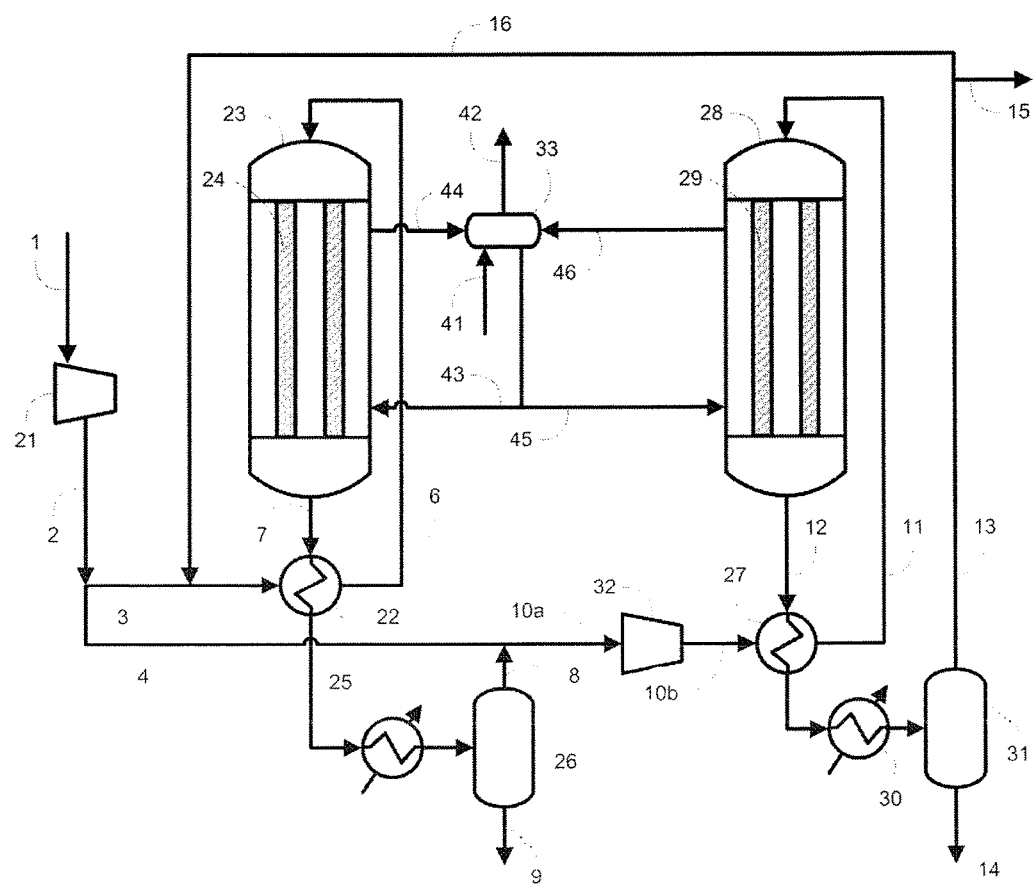

METHOD FOR PRODUCING METHANOL AND APPARATUS FOR PRODUCING METHANOL

TECHNICAL FIELD

The present invention relates to a method for producing methanol and an apparatus for producing methanol.

BACKGROUND ART

Industrial production of methanol is performed by using a fossil fuel as a feedstock, and by allowing a synthesis gas (hereinafter, also referred to as a "synthesis raw material gas" or "raw material gas") mainly comprising carbon monoxide, carbon dioxide and hydrogen, obtained by reforming the fossil fuel, to react on a catalyst. The involved reaction conditions are such that the pressure is 50 to 150 kg/cm², the temperature is 160 to 300° C., and the catalyst used is a catalyst mainly comprising copper/zinc. The methanol synthesis reaction is represented by the following formulas (1) and (2).

[Formula 1]

$$CO+2H_2 \rightarrow CH_3OH \quad (1)$$

$$CO_2+3H_2 \rightarrow CH_3OH+H_2O \quad (2)$$

Patent Document 1 has pointed out a problem that in the methanol synthesis at a low circulation ratio, the reactant partial pressure of the gas is sometimes high, and this causes excessive reaction and the occurrence of overheating of the catalyst bed. Accordingly, Patent Document 1 proposes, in order to solve this problem, that the supplied synthesis raw material gas is divided into two flows, one flow is mixed with the circulation unreacted gas and then introduced into a first synthesis stage, the other flow is mixed with the outlet gas of the first synthesis stage, and before the separation of the synthesized methanol, methanol is synthesized at an additional synthesis stage. The technique disclosed in Patent Document 1 is characterized in that the overheating of a catalyst layer is avoided by regulating the synthesized amount of methanol at the synthesis stage, and at the same time, the circulation ratio represented as the flow rate of the circulation unreacted gas based on the flow rate of the supplied raw material gas can be made as low as 1 to 3.

Patent Document 2 states that the methanol synthesis performed under a low pressure provides an advantage such that the load on a compressor is reduced, or the compressor is made completely unnecessary, but, on the other hand, has a drawback such that a large amount of catalyst is required, or the unreacted gas is required to be recycled at a high circulation ratio. The technique disclosed in Patent Document 2 is characterized in that in order to solve such a drawback, two synthesis reactors are serially installed, and the outlet gas from each of the synthesis reactors is condensed and separated to reduce the circulation ratio so as to be 4.0 or less. Specifically, Examples in Patent Document 2 show that the circulation ratio was altered from 6.0 to 3.5.

Patent Document 3 discloses that higher partial pressures of reactants in reactors can lead to excessive reaction and high temperatures. The document discloses that these high temperatures may lead to a higher deactivation rate for the catalyst. Therefore, Patent Document 3 proposes a technique characterizing in that a plurality of reactors is placed in a synthesis loop; a separator is placed downstream of each of the reactors; the reactant gas can be fed upstream of the reactors and the pressure is increased between the reactors as means for enabling large volumes of the desired product to be produced in an economical manner without a reduction in catalyst life expectancy. Patent Document 3 discloses that the above-described technique enables the production of the desired product to be achieved whilst reducing the circulation rate of gases and controlling the temperatures within the reactors such that an acceptable catalyst life can be achieved. The example of the document indicates that 23% or approximately 28% of the circulation rate of gases is reduced.

However, when the economic efficiency improvement based on scaling up the plant is pursued, there is generally used a technique to achieve a large scale by parallelizing the points at the bottlenecks. For example, in the process of methanol synthesis, the scale of the plant is sometimes limited by, for example, the production restriction imposed on reactors. In such a case, a plurality of reactors is arranged in parallel to achieve a large scale of the whole plant, as the case may be.

Non Patent Document 1 also discloses the considerable degradation of the catalytic activity caused by the water produced by accompanying the methanol synthesis.

Non Patent Document 2 discloses the course of the development of the methanol synthesis technology. More specifically, the development of the production process of the methanol synthesis technology has been advanced with a focus on the pursuance of the improvement of the energy efficiency and the improvement of the economic efficiency on the basis of the achievement of a large scale of plant. Additionally, according to the disclosure in Non Patent Document 2, as effects accompanying a drastic decrease of the circulating amount of the unreacted gas, the reduction of the electric power used and the cooling water amount used, and the size reduction of the piping in a synthesis loop and peripheral devices such as a circulator and heat exchangers are made possible.

CITATION LIST

Patent Documents

Patent Document 1: Japanese Patent No. 4362013
Patent Document 2: Japanese Utility Model Publication No. 51-10210
Patent Document 3: International Publication No. 2006/018610

Non Patent Document

Non Patent Document 1: Applied Catalysis A: General, 469 (2014), p. 306-311
Non Patent Document 2: Masaaki Kuwa, "Advanced Utilization Technology of Natural Gas—Frontier of Development Researches, Chapter 5, Section 2, Methanol Synthesis," supervised by Masaru Ichikawa, N. T. S, 2001, p. 439, pp. 446 to 447.

SUMMARY OF INVENTION

Technical Problem

The synthesis reaction of methanol is represented by the foregoing formulas (1) and (2), and is known to be a number-of-molecules decrease reaction and a highly exothermic reaction. On the other hand, the currently generally used copper/zinc-based catalyst has an appropriate reaction temperature range from 220 to 280° C., and has a drawback that when the reaction temperature is higher than 280° C., the degradation of the catalyst activity, the decrease of the equilibrium methanol concentration and the increase of the unfavorable side reaction products occur. Accordingly, in order to avoid the overheating of the catalyst, it is necessary to establish at least one of the restriction of the reaction amount occurring in the catalyst layer and the cooling of the catalyst layer.

In addition, the heat generated due to the methanol synthesis promotes the sintering of the catalyst, or as disclosed in Non Patent Document 1, the water produced due to the methanol synthesis promotes the degradation of the catalyst. Therefore, in the methanol synthesis, it is demanded that the load on the catalyst is leveled in effectively using the catalyst, and the catalyst is efficiently used.

Considering the global environment, it is demanded to highly maintain the carbon yield in order to reduce the oxidized carbon amount discarded in the methanol production. In addition, as disclosed in Non Patent Document 2, the drastic decrease of the circulating amount of the unreacted gas, namely, the achievement of a low circulation ratio enables the reduction of the electric power used and the cooling water amount used. Accordingly, in the methanol synthesis process, the achievement of the low circulation ratio is also demanded from the viewpoint of the reduction of the energy used. As described above, Patent Document 1 is characterized in that by dividing the amount of the methanol to be synthesized into a plurality of reactors, while the circulation ratio is being made as low as 1 to 3, the catalyst layer temperature can be maintained appropriately. However, in the methanol synthesis reaction, which is an equilibrium reaction with low conversion rate, there is a problem such that in general, the carbon yield is decreased as the circulation ratio is made lower. Actually, when the carbon yield in the methanol synthesis reaction is calculated from the results of Example 2 disclosed in Patent Document 1, the carbon yield is found to be 76.2%, so as to be decreased as compared with Example 1 serving as a comparative example, and thus Example 2 is not practical. Here, the carbon yield is represented by the ratio of the methanol molar flow rate in the crude methanol to the oxidized carbon gases (carbon monoxide and carbon dioxide) molar flow rate in the make-up gas. Patent Document 1 also presents Example 3 as an example of a technique to improve the carbon yield by installing an apparatus which allows a purge gas to further react. However, the installation of an additional reaction apparatus and the units to be attached thereto requires a large scale of facility investment. In addition, in Patent Document 1, as can be seen from the scope of claims and the accompanying drawings, there is no technical idea such that the unreacted gas is separated from the outlet gas of the first synthesis stage, and the unreacted gas is used as a raw material for the next synthesis stage. Instead, in the scope of claims and the accompanying drawings of Patent Document 1, the outlet gas in the first synthesis stage is disclosed to be wholly fed to the second synthesis stage, so as to exclude the above-described technical idea.

Moreover, Patent Document 2 states that a synthesis under low pressure and with a low circulation ratio has been made possible by condensation separation of products including methanol between synthesis reactors. However, in Examples of Patent Document 1, the circulation ratio was altered from 6.0 to 3.5, not to lead to improvement of the carbon yield. When in such a process as disclosed in Patent Document 2, with the intention of improving the yield and reducing the amount of energy used, (1) the synthesis pressure is increased, (2) the catalyst activity is improved, or (3) the circulation ratio is further reduced, unpreferably the deviations of the methanol production amounts of the respective synthesis reactors tend to be augmented, and at the same time, the deviations of the loads on the catalysts also tend to be augmented. When the deviations of the loads on the catalysts are augmented, the differences are caused among the catalyst degradations. Accordingly, when the catalysts are intended to be replaced at the same time, the catalysts used in some synthesis reactors are replaced under the conditions that the service lives of the catalysts are not yet expired. In other words, when the respective catalysts are intended to be replaced when the catalysts reach the desired service lives thereof, the catalyst replacement timings of the respective synthesis reactors are largely different from each other. Consequently, the efficiency of the operations in the methanol production is degraded.

Patent Document 3 discloses that the above-described technique enables the production of the desired product to be achieved whilst reducing the circulation rate of gases and controlling the temperatures within the reactors such that an acceptable catalyst life can be achieved. However, the example of the document only indicates that the circulation rate of gases can be reduced only to 72% or 77% of the prior art, and fails to disclose the carbon yield. Unless considering the carbon yield, the increase of the reactant gas can maintain the methanol production amounts even if the circulation rate of the gases is reduced. Accordingly, the technique disclosed in Patent Document 3 has no innovation.

Furthermore, it is the most favorable for the carbon yield to provide the outlet of the purge gas at the farthest position from the inlet of the make-up gas within the synthesis loop. On the contrary, it is favorable, from the viewpoint of the amount of the gas throughput at the circulator, to arrange the splitting point of the purge gas at just upstream of the circulator within the synthesis loop. The process disclosed in Patent Document 3 increases the pressure of the gas, i.e., the gas discharged from the synthesis loop, which is unnecessary to be pressurized. Such process is not appropriate since the amount of the gas throughput at the circulator is increased and such increase results in the increase of the energy used.

In addition, when the outlet temperature of a cooler, which is not a water cooling heat exchanger but an air fin cooler for the purpose of the reduction of cooling water or the equipment cost, is adjusted to a range from 55° C. to 90° C. to reduce the separation proportion of methanol in a condensation separation step except for the final condensation separation step, the total amount of a condensable gas introduced to a circulator is increased if the circulator is placed downstream of the equipment used in the condensation separation step. Such case is associated with a high probability of generating a condensate liquid in the circulator. The placement of the circulator is not appropriate since the generation of the condensate liquid causes mechanical trouble and energy loss.

Moreover, as disclosed in Non Patent Document 2, in general, the improvement of the methanol synthesis technology as viewed from the aspect of production process has been performed with a focus on the pursuance of the improvement of the energy efficiency and the improvement of the economic efficiency on the basis of the achievement of a large scale of plant. For example, according to Patent Document 1, an object is to increase the methanol production, and it can be seen that the improvement of economic efficiency is demanded. As viewed from such a trend of the improvement of the methanol synthesis technology, the condensation separation of the products between the synthesis stages as disclosed in Patent Document 2 results in the discharge of a large fraction of energy into the environment, so as to go against the current trend. Specifically, in Examples disclosed in Patent Document 2, the circulation gas amount is 3.5 times the raw material gas amount, and the gas amount flowing while being cooled from the outlet of the first synthesis reactor to a separator is 3.5 or more times the raw material gas amount. Accordingly, unpreferably a large amount of gas is required to be cooled, so as to increase the load on the cooler.

With respect to the parallelization performed when the improvement of the economic efficiency is pursued on the basis of the achievement of a large scale of plant, the achievement of a large scale of plant is made possible in the case where the reactors are parallelized because of the increase of the gas amount capable of being introduced into the reactors. However, in general, such a parallelization does not lead to the yield improvement or the reduction of the circulation ratio.

The present invention has been achieved in view of such circumstances as described above, and the technical problem of the present invention is to provide a method for producing methanol and an apparatus for producing methanol in each of which in the synthesis of methanol, the temperature of the catalyst layer is allowed to fall within an appropriate temperature range, the amount of energy used is reduced by reducing the circulation ratio, moreover a high carbon yield is achieved, and additionally the deviations of the loads on the respective catalyst layers are reduced.

Solution to Problem

The present inventors made a diligent study in order to solve the above-described problems. Consequently, the present inventors have perfected the present invention by discovering that by adopting a specific process, the suppression of the catalyst overheating is achieved, and at the same time, it is possible to jointly achieve the improvement of the yield and the reduction of the circulation ratio, and the reduction of the deviations of the loads on the respective catalyst layers. The specific process has a plurality of methanol synthesis steps, and the unreacted gas separated from the reaction mixture produced in a methanol synthesis step is introduced into the successive methanol synthesis step. Moreover, the final unreacted gas separated from the reaction mixture produced in the methanol synthesis step in the final stage, removed partially as a purge gas, pressurized through a circulator, and mixed with a portion of make-up gas is introduced into the first methanol synthesis step, and thus there is formed a synthesis loop allowing the unreacted gas to pass serially through the respective reactors. In addition, the raw material gas is divided to be introduced, at positions in advance of the respective reactors, into the synthesis loop. Specifically, the present invention is as follows.

[1] A method for producing methanol comprising: synthesis steps of synthesizing methanol from a synthesis gas including hydrogen, carbon monoxide and carbon dioxide; and separation steps of separating an unreacted gas from a reaction mixture obtained by passing through one of the synthesis steps, the method including a synthesis loop having at least two of the synthesis steps and at least two of the separation steps, wherein the synthesis loop includes: a first mixing step of obtaining a first mixed gas by increasing a pressure of a residual gas, obtained by removing a purge gas from a final unreacted gas separated from a final reaction mixture in a final separation step subsequent to a final synthesis step, and mixing the residual gas with 10 to 90 mol % of a make-up gas including hydrogen, carbon monoxide and carbon dioxide; a first synthesis step of synthesizing methanol from the first mixed gas; a first separation step of separating a first unreacted gas from a first reaction mixture obtained in the first synthesis step; a second mixing step of obtaining a second mixed gas by mixing the first unreacted gas and at least a fraction of 10 to 90 mol % of the make-up gas; the final synthesis step of finally synthesizing methanol; and the final separation step of separating the final unreacted gas from the final reaction mixture obtained in the final synthesis step, and at least in the final synthesis step, a reaction temperature of a catalyst layer is controlled by indirect heat exchange with pressurized boiling water.

[2] The method for producing methanol according to [1], wherein at least one separation step of the at least two separation steps included in the synthesis loop is a step of separating with a gas-liquid separator a liquid including methanol, produced by cooling the gaseous reaction mixture.

[3] The method for producing methanol according to [1] or [2], wherein the first unreacted gas is mixed with 40 to 70 mol % of the make-up gas.

[4] The method for producing methanol according to any one of [1] to [3], wherein in the first separation step, the first unreacted gas is obtained by separating 35 to 100 mol % of the methanol in the first reaction mixture.

[5] The method for producing methanol according to any one of [1] to [4], wherein in the first separation step, the first unreacted gas is obtained by separating 75 to 96 mol % of the methanol in the first reaction mixture.

[6] The method for producing methanol according to any one of [1] to [5], wherein a circulation ratio, which is a ratio of a molar flow rate of the residual gas obtained by removing the purge gas from the final unreacted gas to a molar flow rate of the make-up gas, is within a range from 0.6 to 2.0.

[7] The method for producing methanol according to [6], wherein the circulation ratio is within a range from 0.8 to 1.5.

[8] The method for producing methanol according to any one of [1] to [7], wherein a temperature of the pressurized boiling water is within a range from 220° C. to 260° C.

[9] The method for producing methanol according to any one of [1] to [8], wherein the final synthesis step is a step of synthesizing methanol from the second mixed gas, or a step of synthesizing methanol from a second unreacted gas or a third mixed gas obtained by mixing the second unreacted gas and a fraction of the make-up gas, the second unreacted gas being separated from a second reaction mixture obtained in the step of synthesizing methanol from the second mixed gas.

[10] The method for producing methanol according to any one of [1] to [9], wherein the final synthesis step is a step of synthesizing methanol from the second mixed gas.

[11] The method for producing methanol according to any one of [1] to [10], wherein a catalyst used in each of the synthesis steps includes copper atoms and zinc atoms in an atomic ratio (copper/zinc) of 2.0 to 3.0, and further includes aluminum atoms.

[12] The method for producing methanol according to any one of [1] to [11], wherein a catalyst used in each of the synthesis steps comprises copper atoms and zinc atoms in an atomic ratio (copper/zinc) of 2.1 to 3.0, and further comprises alumina in a content of 3% to 20% by mass, and is prepared by a production method including: a step of producing a precipitate including copper and zinc by mixing an aqueous solution including copper, an aqueous solution including zinc and an alkali aqueous solution; a step of obtaining a mixture by mixing the precipitate and an alumina hydrate having a pseudo boehmite structure; and a step of molding the mixture so as for the density to be 2.0 to 3.0 g/mL.

[13] The method for producing methanol according to any one of [1] to [12], wherein the proportion of the make-up gas to be mixed with the first unreacted gas is controlled according to a temperature of a reactor in the synthesis step.

[14] The method for producing methanol according to any one of [1] to [13], wherein in each of all of the synthesis steps, a reaction temperature of a catalyst layer is controlled by indirect heat exchange with pressurized boiling water.

[15] An apparatus for producing methanol comprising: reactors for synthesizing methanol from a synthesis gas including hydrogen, carbon monoxide and carbon dioxide; and separators for separating an unreacted gas from a reaction mixture obtained in one of the reactors, the apparatus including a synthesis loop including at least two of the reactors and at least two of the separators, wherein the synthesis loop includes: a first mixing unit obtaining a first mixed gas by increasing through a circulator a pressure of a residual gas, obtained by removing a purge gas from a final unreacted gas separated from a final reaction mixture in a final separator subsequent to a final reactor, and by mixing the residual gas with 10 to 90 mol % of a make-up gas including hydrogen, carbon monoxide and carbon dioxide; a first reactor for synthesizing methanol from the first mixed gas; a first separator for separating a first unreacted gas from a first reaction mixture obtained in the first reactor; a second mixing unit for obtaining a second mixed gas by mixing the first unreacted gas and 10 to 90 mol % of the make-up gas; the final reactor for finally synthesizing methanol; and the final separator for separating the final unreacted gas from the final reaction mixture obtained in the final reactor, and at least in the final reactor, a reaction temperature of a catalyst layer is controlled by indirect heat exchange with pressurized boiling water.

[16] The apparatus for producing methanol according to [15], further comprising a steam drum, wherein in the first reactor, a reaction temperature of a catalyst layer is controlled by indirect heat exchange with the pressurized boiling water; and at least a fraction of the pressurized boiling water is circulated between both the final reactor and the first reactor, and the steam drum.

[17] The apparatus for producing methanol according to [15], further comprising at least two steam drums, wherein at least a fraction of the pressurized boiling water is circulated between the final reactor and at least one of the two steam drums; and in the first reactor, a reaction temperature of a catalyst layer is controlled by indirect heat exchange with the pressurized boiling water; and at least a fraction of the pressurized boiling water is circulated between the first reactor and at least the other one of the two steam drums.

[18] The apparatus for producing methanol according to any one of [15] to [17], wherein the final reactor is a reactor synthesizing methanol from the second mixed gas, or a reactor synthesizing methanol from a third mixed gas obtained by mixing a second unreacted gas with the make-up gas, the second unreacted gas being separated from a second reaction mixture obtained from the reactor for synthesizing methanol from the second mixed gas.

Advantageous Effects of Invention

According to the present invention, it is possible to provide a method for producing methanol and an apparatus for producing methanol in each of which in the synthesis of methanol, the temperature of the catalyst layer is allowed to keep within an appropriate temperature range, the amount of energy used is reduced by reducing the circulation ratio, moreover a high carbon yield is achieved, and additionally the deviations of the loads on the respective catalyst layers are reduced.

BRIEF DESCRIPTION OF DRAWINGS

FIG. 1 is a schematic diagram illustrating an example of the production apparatus used for the method for producing methanol of the present invention;

FIG. 2 is a schematic diagram illustrating an example of the production apparatus used for the method for producing methanol corresponding to a Comparative Example;

FIG. 3 is a schematic diagram illustrating another example of the production apparatus used for the method for producing methanol of the present invention;

FIG. 4 is a schematic diagram illustrating another example of the production apparatus used for the method for producing methanol corresponding to a Comparative Example;

FIG. 5 is a schematic diagram illustrating another example of the production apparatus used for the method for producing methanol corresponding to a Comparative Example;

FIG. 6 is a schematic diagram illustrating yet another example of the production apparatus used for the method for producing methanol of the present invention; and FIG. 7 is a schematic diagram illustrating yet another example of the production apparatus used for the method for producing methanol corresponding to a Comparative Example.

DESCRIPTION OF EMBODIMENTS

Hereinafter, the mode for carrying out the present invention (hereinafter, simply referred to as the present embodiment) is described in detail with reference to the accompanying drawings if necessary, but the present invention is not limited to the following present embodiment. The present invention can be modified in various ways within the scope not departing from the gist of the present invention. In the accompanying drawings, the same elements will be denoted by the same symbols, and the duplicated descriptions will be omitted. The positional relations such as up, down, left and right are based on the positional relations shown in the drawings, unless otherwise specified. Moreover, the dimensional proportions in the drawings are not limited to the proportions shown in the drawings.

The method for producing methanol of the present embodiment is a method for producing methanol including: a synthesis step of synthesizing methanol from a synthesis gas including hydrogen, carbon monoxide and carbon dioxide; and a separation step of separating an unreacted gas from a reaction mixture obtained by passing through the synthesis step, the method including a synthesis loop having at least two synthesis steps and at least two separation steps, wherein the synthesis loop includes: a first mixing step of obtaining a first mixed gas by increasing through a circulator a pressure of a residual gas, obtained by removing a purge gas from a final unreacted gas separated from a final reaction mixture in a final separation step subsequent to a final synthesis step, and by mixing the residual gas with 10 to 90 mol %, preferably 10 to 70 mol % of a make-up gas including hydrogen, carbon monoxide and carbon dioxide; a first synthesis step of synthesizing methanol from the first mixed gas; a first separation step of separating a first unreacted gas from the first reaction mixture obtained in the first synthesis step; a second mixing step of obtaining a second mixed gas by mixing the first unreacted gas and at least a fraction of 10 to 90 mol %, preferably 30 to 90 mol % of the make-up gas; the final synthesis step of finally synthesizing methanol; and the final separation step of separating the final unreacted gas from the final reaction mixture obtained in the final synthesis step, and at least in the final synthesis step, the reaction temperature of a catalyst layer is controlled by indirect heat exchange with pressurized boiling water.

The apparatus for producing methanol of the present embodiment is an apparatus used for the above-described method for producing methanol. More specifically, the apparatus for producing methanol of the present embodiment is an apparatus for producing methanol including: a reactor synthesizing methanol from a synthesis gas including hydrogen, carbon monoxide and carbon dioxide; and a separator separating the unreacted gas from the reaction mixture obtained in the reactor, the apparatus including a synthesis loop including at least two reactors and at least two separators, wherein the synthesis loop includes: a first mixing unit obtaining a first mixed gas by increasing through a circulator a pressure of a residual gas, obtained by removing a purge gas from a final unreacted gas separated from a final reaction mixture in a final separator subsequent to a final reactor, and by mixing the residual gas with 10 to 90 mol %, preferably 10 to 70 mol % of a make-up gas including hydrogen, carbon monoxide and carbon dioxide; a first reactor synthesizing methanol from the first mixed gas; a first separator separating a first unreacted gas from the first reaction mixture obtained in the first reactor; a second mixing unit obtaining a second mixed gas by mixing the first unreacted gas and at least a fraction of 10 to 90 mol %, preferably 30 to 90 mol % of the make-up gas; the final reactor finally synthesizing methanol; and the final separator separating the final unreacted gas from the final reaction mixture obtained in the final reactor, and at least in the final reactor, the reaction temperature of a catalyst layer is controlled by indirect heat exchange with pressurized boiling water.

In the present embodiment, at least one separation step is disposed in the fore stage of the final synthesis step. In the present embodiment, in at least one separation step other than the final separation step, the reaction product including methanol and the unreacted synthesis gas (hereinafter, referred to as the "unreacted gas") are separated from the reaction mixture obtained from the immediately preceding synthesis step, and methanol is synthesized in the synthesis step in the subsequent stage from the mixed gas obtained by mixing the unreacted gas with the make-up gas.

(Synthesis Loop)

In the present embodiment, the synthesis loop is formed in the following way: the gas passing through at least one synthesis step and at least one separation step passes through the final synthesis step and the final separation step, and the unreacted gas separated in the final separation step is used through a circulator as the raw material gas in the first synthesis step. As the material entering of the material entering into and exiting from the synthesis loop, the make-up gas is divided into a plurality of flows, and then the plurality of flows is introduced into the synthesis loop from the mixing steps in advance of the respective synthesis steps. As the material exiting of the material entering and exiting, the reaction product in the reaction mixture is separated in the separation step and extracted to outside the synthesis loop, and a fraction of the unreacted gas separated in the final separation step subsequent to the final synthesis step is taken out to outside the synthesis loop as the purge gas. In the present specification, the "reaction mixture" is the outlet component of the synthesis step, namely, a mixture comprising the component produced from the reaction in the synthesis step and the unreacted component, and usually includes methanol.

Here, the outlet of the purge gas in the synthesis loop is positioned preferably at the point of lower pressure in the synthesis loop, more preferably at the point just upstream of the circulator from the viewpoint of reducing the amount of the gas throughput at the circulator. On the contrary, from the viewpoint of the carbon yield, a fraction of the unreacted gas obtained by separating the reaction product from the reaction mixture and discharging the reaction product to the outside of the synthesis loop is preferably divided as a purge gas, and more preferably the outlet of the purge gas is positioned at the point upstream of mixing section of the make-up gas. In Patent Document 3, as a result of placing the circulator between reactors, the position of the circulator is not appropriate since the circulator increases the pressure of the gas including the purge gas.

The unreacted gas in each of the separation steps is introduced into the subsequent mixing step, synthesis step and separation step, and the respective unreacted gases form the synthesis loop, capable of being serially introduced into all the reactors.

The final synthesis step is not particularly limited, and can be any step that synthesizes methanol from the mixed gas obtained by mixing the unreacted gas and the make-up gas, the unreacted gas being separated from the reaction mixture passing through the synthesis steps synthesizing methanol subsequently to the first synthesis step. The final synthesis step is preferably a step (the second synthesis step) of synthesizing methanol from the second mixed gas. Alternatively, the final synthesis step is also preferably a step (the third synthesis step) of synthesizing methanol from the third mixed gas obtained by mixing the second unreacted gas and the make-up gas, the second unreacted gas being separated from the second reaction mixture obtained in the second synthesis step. Of the second synthesis step and the third synthesis step, the final synthesis step is more preferably the second synthesis step.

The final separation step is not particularly limited, and can be any step that separates the unreacted gas from the reaction mixture subsequently to the first separation step. The final separation step is preferably the second separation step of separating the second unreacted gas from the second reaction mixture obtained in the second synthesis step. Alternatively, the final separation step is preferably the third separation step of separating the third unreacted gas from the third reaction mixture obtained in the third synthesis step. Of the second separation step and the third separation step, the final separation step is more preferably the second separation step.

(Make-Up Gas)

The make-up gas is a gas obtained by increasing the pressure of a synthesis raw material gas including carbon monoxide (CO), carbon dioxide ($CO_2$) and hydrogen ($H_2$) such as a steam reformed gas of natural gas or coal gasification gas, to the reaction pressure by using a compressor. The reaction pressure may be, for example, 4.9 to 14.7 MPa-G (50 to 150 kg/cm$^2$-G), is more preferably 7.8 to 10.8 MPa-G (80 to 110 kg/cm$^2$-G). Industrially, the make-up gas is obtained, for example, by the steam-reforming reaction using natural gas as a raw material, and the relation (M) among the mol % values of CO, $CO_2$ and $H_2$ derived from the following formula is preferably larger than 1.0 and 2.0 or less, and more preferably 1.3 to 1.5:

$$M=(H_2 \text{ mol \%})/(2\times CO \text{ mol \%}+3\times CO_2 \text{ mol \%})$$

(Division of Make-Up Gas)

In the present embodiment, the make-up gas is divided into a plurality of flows before being introduced into the synthesis loop, and introduced into the synthesis loop as a fraction of the raw material gas in the plurality of synthesis steps present in the synthesis loop. The preferable ranges of the division proportions of the make-up gas are different depending on the synthesis conditions in the respective synthesis steps and the separation conditions in the respective separation steps. However, the molar flow rate of the make-up gas included in the mixed gas (the first mixed gas) supplied to the first methanol synthesis step (the first synthesis step) is 10 to 90 mol %, preferably 10 to 70 mol % based on the total amount of the make-up gas. The molar flow rate of the make-up gas included in the mixed gas (the second mixed gas) supplied to the second methanol synthesis step (the second synthesis step) is 10 to 90 mol %, preferably 10 to 70 mol % based on the total amount of the make-up gas. If the third or later methanol synthesis step is present and the total molar flow rate of the make-up gas supplied to the first and second synthesis steps is less than 100 mol %, the residual make-up gas is appropriately divided to be supplied to the respective third or later methanol synthesis steps. If the third or later methanol synthesis step is present and the total molar flow rate of the make-up gas supplied to the first and second synthesis steps is 100 mol %, the make-up gas is not supplied to the respective third or later methanol synthesis steps. For example, as an embodiment, here is described a case of a production method using a condensation separation method as the separation method in the separation step and having two synthesis steps and two condensation separation steps. In this embodiment, in a case where the temperature of the outlet gas of the first condensation separation step is set at 20° C. to 100° C., the proportion of the make-up gas (the proportion based on the total amount of the make-up gas; the same also applies hereinafter) introduced into the synthesis loop immediately in advance of the final synthesis step (the second synthesis step) is preferably 10 to 90 mol %, more preferably 30 to 90 mol % and further preferably 40 to 70 mol %, for example, from the viewpoint of the carbon yield and the highest temperature of the catalyst layer. In addition, in a case where the temperature of the outlet gas of the first condensation separation step is set at 40° C. to 80° C., the proportion of the make-up gas introduced into the synthesis loop immediately in advance of the final synthesis step may be 10 to 90 mol %, preferably 30 to 90 mol %, more preferably 40 to 70 mol % and furthermore preferably 45 to 65 mol %, from the same viewpoint as described above.

The synthesis gas serving as the raw material gas for the synthesis step is supplied to the synthesis step after being preferably heated to 180 to 260° C. with a preheater. The synthesis gas temperature when supplied to the synthesis step is appropriately set according to, for example, the type and amount of the catalyst, the type of the reactor and the reaction pressure, and the preferable synthesis gas temperature is 200 to 230° C.

The proportion (division proportion) of the make-up gas mixed in the unreacted gas in the mixing step is preferably regulated according to the desired temperatures of the respective reactors in the synthesis step. The desired temperatures as referred to herein mean the temperatures in the methanol synthesis reaction described later.

In the present embodiment, the make-up gas is divided into a plurality of flows before the make-up gas is introduced into the synthesis loop, and the division proportions of the plurality of flows can be adjusted. Accordingly, the temperatures of the reactors in the synthesis steps can be easily controlled.

(Synthesis Step and Catalyst)

In the synthesis step, methanol is synthesized from the synthesis gas. The reactor used in the synthesis step preferably includes, in addition to a catalyst layer, a mechanism (heat-removing mechanism) for removing the heat produced by the reaction from the catalyst layer.

The catalyst used in the synthesis is preferably a methanol synthesis catalyst including copper atoms and zinc atoms as the essential components. Such a catalyst is reduced from the state of oxide by a reducing gas such as hydrogen or carbon monoxide, or a mixed gas comprising hydrogen and carbon monoxide, and consequently the copper is activated to give catalytic activity to the catalyst. The catalyst may also include, in addition to the copper atoms and the zinc atoms, aluminum atoms and/or chromium atoms as the main third component. The catalyst including copper and zinc as the essential components can be prepared by heretofore known methods. Such a catalyst can be prepared by the methods disclosed in, for example, Japanese Utility Model Publication No. 51-44715, Japanese Patent No. 2695663, Japanese Utility Model Publication No. 06-35401, Japanese Patent Application Laid-Open No. 10-272361, and Japanese Patent Application Laid-Open No. 2001-205089.

A preferable catalyst is a methanol synthesis catalyst including the copper atoms and the zinc atoms in an atomic ratio (copper/zinc) of 2.0 to 3.0, and additionally aluminum atoms. Examples of such a catalyst include the catalysts prepared by the method disclosed in Japanese Patent Application Laid-Open No. 08-299796, and the catalyst disclosed in International Publication No. WO 2011/048976.

Examples of a preferable catalyst include the catalysts used in Examples and Comparative Examples such as Example 2 and Example 3 in International Publication No. 2011/048976. The more preferable atomic ratio (copper/zinc) of the copper atoms and the zinc atoms in the catalyst falls within a range from 2.1 to 3.0. The methanol synthesis catalyst additionally including alumina in a content of 3 to 20% by mass is furthermore preferable. As described above, such a catalyst can be prepared by, for example, the method disclosed in International Publication No. 2011/048976. More specifically, such a catalyst is prepared by, for example, a production method including: a step of producing a precipitate including copper and zinc by mixing an aqueous solution containing copper and an aqueous solution containing zinc and an alkaline aqueous solution; a step of obtaining a mixture by mixing the obtained precipitate and an alumina hydrate having a pseudo boehmite structure; and a step of molding the obtained mixture so as to have a density of 2.0 to 3.0 g/mL. Examples of the molding method include tableting, extrusion molding and tumbling granulation. However, the catalyst used in the present embodiment is not limited to the above-described catalyst and the catalyst prepared by the above-described preparation method, and may also be other catalysts having the equivalent methanol synthesis activity.

The method for removing heat from the catalyst layer is preferably a method for indirectly exchanging heat between the catalyst layer and pressurized boiling water by using pressurized boiling water as a coolant. Here, the pressurized boiling water means the water boiling so as to utilize the latent heat in the removal of heat from the catalyst layer. Examples of the heat-removing mechanism related to such a heat-removing method include: a cooling mechanism allowing pressurized boiling water to flow in a counter-flow direction or a co-current flow direction in relation to the gas flow direction in the catalyst layer; and a cooling mechanism allowing pressurized boiling water to flow in a direction perpendicular to the gas flow direction in the catalyst layer. More specifically, examples of the above-described heat-removing mechanism include: a multitubular reactor having inner tubes parallel to the gas flow direction of the catalyst layer, forming a catalyst layer on the inside of the inner tubes and allowing a coolant to flow on the outside of the inner tubes; the multitubular reactor having the inner tubes parallel to the gas flow direction of the catalyst layer, forming the catalyst layer on the outside of the inner tubes, and allowing the coolant to flow on the inside of the inner tubes; and an interlayer cooling reactor allowing the coolant to flow in the inner tubes disposed so as to be perpendicular to the gas flow direction of the catalyst layer. The temperature of the pressurized boiling water serving as the coolant is preferably 210 to 260° C. The use of the steam produced from the pressurized boiling water is preferably the use as the raw material steam for the steam-reforming reaction of the natural gas. In this case, the pressure of the pressurized boiling water preferably has a pressure higher than the pressure (1.5 to 2.5 MPa-G (15 to 25 kg/cm²-G)) of the common steam-reforming reaction, and hence the temperature of the pressurized boiling water is more preferably, for example, 220 to 240° C.

The control of the reaction temperature of the catalyst layer by the indirect heat exchange with the pressurized boiling water may be performed at least in the final synthesis step; however, it is preferable to control the reaction temperature of the catalyst layer by the indirect heat exchange with the pressurized boiling water in all the synthesis steps. When the pressurized boiling water is used as the coolant in a plurality of reactors, the temperatures of the pressurized boiling water in the respective reactors may be the same as each other or may be different from each other.

The methanol synthesis reaction in the synthesis step is, as is well known, preferably performed under the conditions that the pressure is 4.9 to 14.7 MPa-G (50 to 150 kg/cm²-G) and the temperature is 200 to 300° C. The pressure and the temperature in the methanol synthesis reaction are more preferably 7.8 to 10.8 MPa-G (80 to 110 kg/cm²-G) and 200 to 280° C., respectively, and furthermore preferably 7.8 to 10.8 MPa-G (80 to 110 kg/cm²-G) and 200 to 270° C., respectively.

When a plurality of reactors has the same catalyst amount, the ratio of the maximum amount to the minimum amount of the methanol production amounts in the respective methanol synthesis steps is preferably 1 to 3 and more preferably 1 to 2.

(Separation Step)

In the separation step, the unreacted gas is separated from the reaction mixture including the reaction product obtained in the synthesis step. In other words, methanol or methanol and water and the unreacted gas included in the reaction mixture are separated. Examples of the separation method include: a condensation separation method in which the outlet gas from the synthesis step is cooled, and the condensed liquid produced by cooling is separated with a gas-liquid separator; and a membrane separation method using a separation membrane, among these the condensation separation method is preferable. In the present embodiment, at least two separation steps (condensation separation steps) using the condensation separation method are provided within the synthesis loop, and one of these steps is preferably the final condensation separation step subsequent to the final synthesis step. The fluid cooled in the condensation separation step is the outlet gas (gaseous reaction mixture) from the synthesis step preceding the condensation separation step, and the outlet gas includes the synthesized methanol. Examples of the method for obtaining the liquid including methanol as a condensed liquid include: an air cooling based on the mutual heat exchange with the synthesis gas supplied to the reactor or an air cooling with an air fin cooler; and a cooling with a coolant such as cooling water or brine. According to the initial temperature before cooling and the target temperature after cooling of the fluid (reaction mixture) being an object to be cooled, the methods for obtaining the condensed liquid are used each alone or in combinations of two or more thereof. In general, the obtained condensed liquid is separated by using a gas-liquid separator (hereinafter, also simply referred to as the "separator"). In combining these coolers (condensers) and separators, a combination of one of these coolers and one of these separators may be adopted, or alternatively, a combination of two or more of these cooler and two or more of these separators may also be adopted. Examples of the combination of two or more of these cooler and two or more of these separators include the combination disclosed in Japanese Patent Application Laid-Open No. 61-257934. More specifically, examples of the above-described combinations include a method in which when the reaction mixture obtained by passing through the synthesis step is cooled, and the reaction product mainly comprising methanol is condensed and separated, the condenser is divided into two stages, the heat transfer surface temperature of the first-stage condenser is set at a temperature equal to or lower than the dew point of the reaction mixture and equal to or higher than the melting point of the paraffins included in the reaction mixture, and the heat transfer surface temperature of the second-stage condenser is set at 60° C. or lower.

For example, as an embodiment, here is described a case of a production method using a condensation separation method as the separation method in the separation step, and having two synthesis steps and two condensation separation steps. The first condensation separation step is the step of condensing and separating the outlet gas (gaseous reaction mixture) from the first synthesis step, and is arranged subsequently to the first synthesis step. The first condensation separation step extracts methanol from the synthesis loop by separating preferably 35 to 100 mol %, more preferably 35 to 99 mol %, and furthermore preferably 75 to 96 mol % of the methanol included in the outlet gas from the first synthesis step.

In the condensation separation step, the reaction mixture is cooled until a predetermined amount of the condensed liquid including methanol or methanol and water is produced by cooling. For example, when the fluid (reaction mixture) having a methanol partial pressure of 0.69 to 0.88 MPa-G (7.0 to 9.0 kg/cm²-G) is cooled and condensed, the fluid is cooled preferably at 20 to 100° C. and more preferably at 40 to 80° C. In this case, from the viewpoint of improving the methanol yield, in the first condensation separation step, the separation proportion of the methanol included in the outlet gas from the first synthesis step is preferably set at higher than 75 mol %. Moreover, for the reaction control in the subsequent second synthesis step, in the first condensation separation step, the separation proportion of the methanol included in the outlet gas from the first synthesis step is more preferably set at lower than 96 mol %. From the viewpoint of saving the cooling water, the cooling in the first condensation separation step preferably uses only the cooling (air cooling) with an air fin cooler. In this case, the target temperature of the reaction mixture after cooling is preferably 55 to 90° C. from the same viewpoint as described above.

As described above, by providing separation steps between a plurality of synthesis steps, the amounts of water supplied to the reactors are reduced in the synthesis steps subsequent to the separation steps. Consequently, as compared with the case where no separation steps are involved, the sintering of the copper particles considered to be the active sites of the catalyst is suppressed, and hence the effect of extending the catalyst service life is assumed. By providing separation steps between a plurality of synthesis steps, and by using the unreacted gas separated in a separation step as the raw material for the synthesis step subsequent to the separation step, the balance between the reaction amounts in the synthesis steps respectively preceding to and subsequent to the separation step concerned is made satisfactory, and consequently the catalysts can be used more effectively. Moreover, in the separation steps between the plurality of synthesis steps, by supplying to the synthesis step subsequent to one of the separation steps the outlet gas from the synthesis step preceding to the separation step concerned without separating 4 to 25 mol % of the methanol included in the outlet gas, the reaction in the subsequent synthesis step can be controlled and the overheating of the catalyst layer can also be suppressed. In this case, the amount of the condensable gas which is not removed in the separation step is increased. Therefore, it is not appropriate to place the circulator between the separator used in the separation step and the subsequent reactor and to increase the pressure of the gas since the condensate in the circulator becomes increasingly likely to be generated by the arrangement.

The outlet gas from the final synthesis step is supplied to the final separation step. The final separation step separates preferably 80 to 96 mol %, more preferably 93 to 96 mol % of the methanol included in the outlet gas (gaseous reaction mixture) from the final synthesis step. When the condensation separation is adopted in the final separation step, the outlet gas from the final synthesis step is cooled preferably to 20° C. to 50° C., for example to 45° C., and is separated into the gas phase (the unreacted gas) and the liquid phase with a gas-liquid separator. A fraction of the unreacted gas (final unreacted gas) separated as the gas phase component in the gas-liquid separator is removed as a purge gas to outside the system, and the residual unreacted gas is increased in the pressure thereof to the reaction pressure as the circulation gas by passing through the circulator, and then supplied to the first synthesis step. The extraction of a fraction of the gas as the purge gas to outside the synthesis loop is for the purpose of removing the inert component accumulating in the synthesis loop. In this case, the flow rate of the purge gas may be appropriately adjusted in such a way that the below described circulation ratio falls within a desired numerical value range. Here, the circulation ratio is defined by the ratio of the molar flow rate of the circulation gas to the molar flow rate of the make-up gas. In the present embodiment, the molar flow rate of the circulation gas is the molar flow rate of the remaining gas obtained by removing the purge gas from the final unreacted gas. The reaction products including methanol separated in the respective separation steps in the synthesis loop are taken out as crude methanol.

The outlet of the purge gas in the synthesis loop is positioned preferably at the point of lower pressure in the synthesis loop, more preferably at the point just upstream of the circulator from the viewpoint of reducing the amount of the gas throughput at the circulator. In addition, from the viewpoint of the carbon yield, a fraction of the unreacted gas obtained by separating the reaction product from the reaction mixture and discharging the reaction product to the outside of the synthesis loop is preferably divided as a purge gas, and more preferably the outlet of the purge gas is positioned upstream of mixing section of the make-up gas. Furthermore, in each of the separation steps between a plurality of the synthesis steps, by supplying 4 to 25 mol % of methanol included in the outlet gas from the synthesis step in advance of the separation step without separating from the outlet gas, it is possible to control the reaction and prevent the overheat of the catalyst layer in the synthesis step after the separation step. In this case, it is not appropriate to place the circulator downstream of the separator used in the separation step and upstream of the reactor used in the subsequent synthesis step since the condensate may be generated in the circulator.

From the viewpoint of these, it is preferable to place the circulator so as to recycle the residual gas after removing the purge gas from the unreacted gas after the final separation step to the point of mixing the residual gas in the first mixing step.

The circulation ratio in the methanol synthesis process is defined by the ratio of the molar flow rate of the circulation gas to the molar flow rate of the make-up gas. In the present embodiment, the circulation ratio is preferably 0.6 or more and 2.0 or less and more preferably 0.8 or more and 1.5 or less. In comparison of the gas composition of the make-up gas and the gas composition of the circulation gas, the make-up gas is higher in the content proportions of carbon monoxide and carbon dioxide, the raw materials for the methanol synthesis, an exothermic reaction, and hence more tends to generate heat in the catalyst layer. Accordingly, by setting the circulation ratio at 0.6 or more, the overheating of the catalyst mainly due to the make-up gas can be further suppressed through the dilution due to the circulation gas. On the other hand, by setting the circulation ratio at 2.0 or less, the energy efficiency in the whole process is improved. This is because the relative increase of the molar flow rate of the make-up gas allows the molar flow rate of hydrogen or the like, intrinsically needing no cooling, to be reduced, and correspondingly, the load on the cooler can be reduced.

In the method for producing methanol of the present embodiment, the synthesis loop may have three or more mixing steps, three or more synthesis steps and three or more separation steps.

FIG. 1 is a schematic diagram illustrating an example of the production apparatus used for the method for producing methanol of the present embodiment. The production apparatus is an apparatus for producing methanol, including reactors 23 and 28 each synthesizing methanol from a synthesis gas including hydrogen, carbon monoxide and carbon dioxide, and gas-liquid separators 26 and 31 being the separators separating the unreacted gases from the reaction mixtures obtained in the reactors 23 and 28, respectively. The apparatus for producing methanol includes a synthesis loop including the two reactors 23 and 28 and the two gas-liquid separators (separators) 26 and 31, wherein the synthesis loop includes: a first mixing unit (the mixing section of a line 5 and a line 3) obtaining a first mixed gas by increasing through a circulator 32 a pressure of a residual gas obtained by removing a purge gas from the second unreacted gas separated from the second reaction mixture in the second gas-liquid separator 31 subsequent to the second reactor 28, and by mixing the residual gas with 10 to 90 mol % of the make-up gas including hydrogen, carbon monoxide and carbon dioxide; the first reactor 23 synthesizing methanol from the first mixed gas; a first gas-liquid separator 26 separating the first unreacted gas from the first reaction mixture obtained in the first reactor 23; the second mixing unit (the mixing section of a line 4 and a line 8) obtaining the second mixed gas by mixing the first unreacted gas and the 10 to 90 mol % of the make-up gas; the second reactor 28 finally synthesizing methanol from the second mixed gas; and the second gas-liquid separator 31 separating the second unreacted gas from the second reaction mixture obtained in the second reactor 28, and in the reactors 23 and 28, the reaction temperatures of the catalyst layers in inner tubes 24 and 29 are controlled by the indirect heat exchange with pressurized boiling water. In the present embodiment, the second reactor 28, the second gas-liquid separator 31, the second reaction mixture and the second unreacted gas correspond to the final reactor, the final separator, the final reaction mixture and the final unreacted gas, respectively.

The synthesis raw material gas including CO, $CO_2$ and $H_2$, produced by steam-reforming reaction is introduced into the system from a line 1, and is increased in pressure to a predetermined pressure with a compressor 21. A predetermined amount of the synthesis raw material gas (make-up gas) increased in pressure is allowed to flow in the line 3, mixed with the circulation gas from the line 5, and then supplied to a preheater 22. The mixed synthesis gas (mixed gas) is subjected to the heat exchange, in the preheater 22, with the outlet gas (reaction mixture) including the reaction product flowing in a line 7 of the outlet of the reactor 23, to be preheated to a predetermined temperature, and supplied to the reactor 23 from a line 6. The residual make-up gas flows in the line 4.

The reactor 23 has the inner tubes 24 preferably made of a carbon steel, and the methanol synthesis catalyst including copper and zinc as the essential components is filled in the inner tubes 24 to form the catalyst layer. Methanol is synthesized in the process allowing the synthesis gas supplied from the line 6 into the reactor 23 to pass through the catalyst layer in the inner tubes 24. The pressure and the temperature of the fluid in the catalyst layer are only required to fall within the pressure range and the temperature range in the above-described methanol synthesis reaction, respectively.

The outlet gas (reaction mixture) including methanol, flowing out from the reactor 23 into the line 7, is cooled in the preheater 22, and then further cooled by a condenser 25 to a temperature equal to or lower than the dew point of methanol, to promote the condensation of methanol. In the fluid including the condensed methanol, the condensed fraction thereof is extracted in the gas-liquid separator 26 as crude methanol from a line 9 to outside the system, and the residual gas phase fraction thereof flows in the line 8.

The fraction of the make-up gas, having flowed in the line 4 is mixed with the unreacted gas having flowed from the gas-liquid separator 26 in the line 8, and then supplied to the reactor 28 from a line 11 by way of a line 10 and a preheater 27.

The synthesis gas flowing in the line 10 is preheated to a predetermined temperature by being subjected to the heat exchange, in the preheater 27, with the outlet gas including the reaction product, flowing in a line 12 of the outlet of the reactor 28. The reactor 28 has the inner tubes 29 preferably made of a carbon steel, and the methanol synthesis catalyst including copper and zinc as the essential components is filled in the inner tubes 29 to form the catalyst layer. Methanol is synthesized in the process allowing the synthesis gas supplied from the line 11 into the reactor 28 to pass through the catalyst layer in the inner tubes 29. The pressure and the temperature of the fluid in the catalyst layer are only required to fall within the pressure range and the temperature range in the above-described methanol synthesis reaction, respectively.

The outlet gas (reaction mixture) including methanol, flowing out from the reactor 28 into the line 12, is cooled in the preheater 27, and then further cooled by a condenser 30 to a predetermined temperature, to further condense methanol. In the fluid including the condensed methanol, the condensed fraction thereof is extracted in the gas-liquid separator 31 as crude methanol from a line 14 to outside the system, and the residual gas phase fraction (unreacted gas) thereof flows in a line 13. Of the unreacted gas flowing in the line 13, the unreacted gas of an amount to give a predetermined circulation ratio passes as the circulation gas through a line 16 and a circulator 32, and merges from the line 5 with the make-up gas flowing in the line 3, to be recycled to the reactor 23. The residual unreacted gas is extracted as a purge gas from the synthesis loop to outside the system from a line 15, in order to remove the inert component accumulating in the synthesis loop.

The cooling of the catalyst layers in the reactor 23 and the reactor 28 is performed in the process in which the boiler water from the steam drum 33 is introduced from lines 43 and 45 into the respective reactors 23 and 28, the introduced boiler water is used as pressurized boiling water, and the fluids including the produced steam are collected respectively from lines 44 and 46 in the steam drum 33. The steam produced by the reaction heat is taken out from the steam drum 33 into a line 42, and water of an amount to compensate the steam amount is supplied from a line 41 to the steam drum 33. The steam taken out from the line 42 can be used as the raw material steam necessary for the steam-reforming reaction in the production of the raw material gas from natural gas.

FIG. 3 is a schematic diagram illustrating another example of the production apparatus used for the method for producing methanol of the present embodiment.

The difference from the production apparatus shown in FIG. 1 is in that the steam drum of the boiler water used for cooling the catalyst layer was provided for each of the reactors. Specifically, the cooling of the catalyst layer in the reactor 23 is performed in the process in which the boiler water from the steam drum 33 is introduced from the line 43 into the reactor 23, the boiler water is used as pressurized boiling water, and the fluid including the produced steam is collected from the line 44 in the steam drum 33. The steam produced by the heat of reaction is taken out from the steam drum 33 to the line 42, and water of an amount to compensate the steam amount is supplied from the line 41 to the steam drum 33. On the other hand, the cooling of the catalyst layer in the reactor 28 is performed in the process in which the boiler water from the steam drum 34 is introduced from the line 45 into the reactor 28, and the fluid including the produced steam is collected from the line 46 in the steam drum 34. The steam produced by the heat of reaction is taken out from the steam drum 34 to a line 48, and water of an amount to compensate the steam amount is supplied from a line 47 to the steam drum 34. The steam taken out from the lines 42 and 48 is used as the raw material steam necessary for the steam-reforming reaction in the production of the raw material gas from natural gas.

FIG. 6 is a schematic diagram illustrating yet another example of the production apparatus used for the method for producing methanol of the present embodiment. The difference from the production apparatus shown in FIG. 1 is in that three mixing units, three reactors and three gas-liquid separators are provided. The production apparatus is an apparatus for producing methanol, including reactors 23a, 23b and 23c each synthesizing methanol from a synthesis gas including hydrogen, carbon monoxide and carbon dioxide, and gas-liquid separators 26a, 26b and 26c being the separators separating the unreacted gases from the reaction mixtures obtained in the reactors 23a, 23b and 23c, respectively. The apparatus for producing methanol includes a synthesis loop including the three reactors 23a, 23b and 23c, and the three gas-liquid separators (separators) 26a, 26b and 26c, wherein the synthesis loop includes: a first mixing unit (the mixing section of the line 5 and a line 3a) obtaining a first mixed gas by increasing through the circulator 32 the pressure of the residual gas obtained by removing a purge gas from the third unreacted gas separated from the third reaction mixture in a third gas-liquid separator 26c subsequent to the third reactor 23c, and by mixing the residual gas with 10 to 70 mol % of the make-up gas including hydrogen, carbon monoxide and carbon dioxide; the first reactor 23a synthesizing methanol from the first mixed gas; the first gas-liquid separator 26a separating the first unreacted gas from the first reaction mixture obtained in the first reactor 23a; a second mixing unit (the mixing section of a line 3b and a line 8a) obtaining a second mixed gas by mixing the first unreacted gas with 10 to 70 mol % of the make-up gas; the second reactor 23b synthesizing methanol from the second mixed gas; the second gas-liquid separator 26b separating the second unreacted gas from the second reaction mixture obtained in the second reactor 23b; a third mixing unit (the mixing section of the line 3c and the line 8b) obtaining a third mixed gas by mixing the second unreacted gas with 20 to 80 mol % of the make-up gas; the third reactor 23c finally synthesizing methanol from the third mixed gas; and a third gas-liquid separator 26c separating the third unreacted gas from the third reaction mixture obtained in the third reactor 23c, and in the reactors 23a, 23b and 23c, the reaction temperatures of the catalyst layers in inner tubes 24a, 24b and 24c are controlled by the indirect heat exchange with pressurized boiling water. In the present embodiment, the third reactor 23c, the third gas-liquid separator 26c, the third reaction mixture and the third unreacted gas correspond to the final reactor, the final separator, the final reaction mixture and the final unreacted gas, respectively.

The synthesis raw material gas including CO, $CO_2$ and $H_2$, produced by steam-reforming reaction is introduced into the system from the line 1, and is increased in pressure to a predetermined pressure with the compressor 21. A predetermined amount, another predetermined amount and the residual synthesis raw material gas (make-up gas) increased in pressure flow in the line 3a, the line 3b and a line 3c, respectively. The gas having flowed in the line 3a is mixed with the circulation gas from the line 5, and then supplied to a preheater 22a. The mixed synthesis gas (mixed gas) is subjected to the heat exchange, in the preheater 22a, with the outlet gas (reaction mixture) including the reaction product flowing in a line 7a of the outlet of the reactor 23a, to be preheated to a predetermined temperature, and supplied to the reactor 23a from the line 6a.

The reactor 23a has the inner tubes 24a preferably made of a carbon steel, and the methanol synthesis catalyst including copper and zinc as the essential components is filled in the inner tubes 24a to form the catalyst layer. Methanol is synthesized in the process allowing the synthesis gas supplied from the line 6a into the reactor 23a to pass through the catalyst layer in the inner tubes 24a. The pressure and the temperature of the fluid in the catalyst layer are only required to fall within the pressure range and the temperature range in the above-described methanol synthesis reaction, respectively.

The outlet gas (reaction mixture) including methanol, flowing out from the reactor 23a into the line 7a, is cooled in the preheater 22a, and then further cooled by a condenser 25a to a temperature equal to or lower than the dew point of methanol, to promote the condensation of methanol. In the fluid including the condensed methanol, the condensed fraction thereof is extracted in the gas-liquid separator 26a as crude methanol from a line 9a to outside the system, and the residual gas phase fraction thereof flows in the line 8a.

The fraction of the make-up gas, having flowed in the line 3b is mixed with the unreacted gas having flowed from the gas-liquid separator 26a in the line 8a, and then supplied to the reactor 23b from the line 6b by way of the line 4b and a preheater 22b.

The synthesis gas flowing in the line 4b is preheated to a predetermined temperature by being subjected to the heat exchange, in the preheater 22b, with the outlet gas including the reaction product, flowing in a line 7b of the outlet of the reactor 23b. The reactor 23b has the inner tubes 24b preferably made of a carbon steel, and the methanol synthesis catalyst including copper and zinc as the essential components is filled in the inner tubes 24b to form the catalyst layer. Methanol is synthesized in the process allowing the synthesis gas supplied from the line 6b into the reactor 23b to pass through the catalyst layer in the inner tubes 24b. The pressure and the temperature of the fluid in the catalyst layer are only required to fall within the pressure range and the temperature range in the above-described methanol synthesis reaction, respectively.

The outlet gas (reaction mixture) including methanol, flowing out from the reactor 23b into the line 7b, is cooled in the preheater 22b, and then further cooled by a condenser 25b to promote the condensation of methanol. In the fluid including the condensed methanol, the condensed fraction thereof is extracted in the gas-liquid separator 26b as crude methanol from a line 9b to outside the system, and the residual gas phase fraction thereof flows in a line 8b.

The fraction of the make-up gas, having flowed in the line 3c is mixed with the unreacted gas having flowed from the gas-liquid separator 26b in the line 8b, and then supplied to the reactor 23c from the line 6c by way of the line 4c and a preheater 22c.

The synthesis gas flowing in the line 4c is preheated to a predetermined temperature by being subjected to the heat exchange, in the preheater 22c, with the outlet gas including the reaction product, flowing in a line 7c of the outlet of the reactor 23c. The reactor 23c has the inner tubes 24c preferably made of a carbon steel, and the methanol synthesis catalyst including copper and zinc as the essential components is filled in the inner tubes 24c to form the catalyst layer. Methanol is synthesized in the process allowing the synthesis gas supplied from the line 6c into the reactor 23c to pass through the catalyst layer in the inner tubes 24c. The pressure and the temperature of the fluid in the catalyst layer are only required to fall within the pressure range and the temperature range in the above-described methanol synthesis reaction, respectively.

The outlet gas (reaction mixture) including methanol, flowing out from the reactor 23c into the line 7c, is cooled in the preheater 22c, and then further cooled to a predetermined temperature by a condenser 25c to further condense methanol. In the fluid including the condensed methanol, the condensed fraction thereof is extracted in the gas-liquid separator 26c as crude methanol from a line 9c to outside the system, and the residual gas phase fraction thereof (unreacted gas) flows in the line 8c.

Of the unreacted gas flowing in the line 8c, the unreacted gas of an amount to give a predetermined circulation ratio passes as the circulation gas through the line 16 and the circulator 32, and merges from the line 5 with the make-up gas flowing in the line 3a, to be recycled to the reactor 23a. The residual unreacted gas is extracted as the purge gas from the synthesis loop to outside the system from the line 15, in order to remove the inert component accumulating in the synthesis loop.

The cooling operations of the catalyst layers in the reactors 23a, 23b and 23c are performed in the process in which the boiler waters from steam drums 33a, 33b and 33c are introduced from lines 43a, 43b and 43c into the reactors 23a, 23b and 23c, respectively, these boiler waters are used as the pressurized boiling waters, and the fluids including the produced steams are collected from lines 44a, 44b and 44c in the steam drums 33a, 33b and 33c, respectively. The steams produced by the heats of reaction are taken out from the steam drums 33a, 33b and 33c to lines 42a, 42b and 42c, respectively, and the amounts of water to compensate the amounts of the steams are supplied from lines 41a, 41b and 41c to the respective steam drums. The steam taken out from the lines 42a, 42b and 42c can be used as the raw material steam necessary for the steam-reforming reaction in the production of the raw material gas from natural gas.

EXAMPLES

Hereinafter, the present invention is described in more detail by way of Examples and Comparative Examples of the methanol synthesis plant design, but the present invention is not limited to these Examples and Comparative Examples.

The catalyst used in the methanol synthesis was any one of the following catalysts: the catalyst (the methanol synthesis catalyst A) prepared by the method disclosed in Example 1 of Japanese Utility Model Publication No. 51-44715; the catalyst (the methanol synthesis catalyst B) prepared by the method disclosed in Example 1 of Japanese Patent Application Laid-Open No. 8-299796; the catalyst (the methanol synthesis catalyst C) prepared by the method disclosed in Example 3 of International Publication No. WO 2011/048976; and the catalyst (the methanol synthesis catalyst D) prepared by the method disclosed in Comparative Example 4 of Japanese Patent Application Laid-Open No. 8-299796.

Example 1

In Example 1, the production apparatus shown in FIG. 1 was used. The involved conditions were as follows. Specifically, as the raw material gas, the gas produced by the steam-reforming reaction of natural gas was used, and the synthesis of methanol was performed under the condition of a circulation ratio of 1.0. As the catalysts in the reactors 23 and 28, the methanol synthesis catalyst C was used. The pressure was increased to 9.9 MPa-G (101 kg/cm$^2$-G) with the compressor 21. In a line 3, 40 mol % of the synthesis raw material gas (make-up gas) increased in pressure was allowed to flow, and subjected to the heat exchange with the outlet gas (reaction mixture) including the reaction product flowing in the line 7 of the outlet of the reactor 23, and thus preheated so as for the temperature in the line 6 to be 200° C. The residual make-up gas, namely, 60 mol % of the make-up gas was allowed to flow in the line 4. As the reactor 23, a reactor having the inner tubes 24 made of a carbon steel was used. In the catalyst layer, the pressure of the fluid was 9.8 to 9.9 MPa-G (100 to 101 kg/cm$^2$-G), and the temperature was between 200 and 262° C.

The outlet gas from the first synthesis step was cooled with the condenser 25 to a temperature equal to or lower than the dew point of methanol, namely, 45° C. (total pressure: 9.6 MPa-G (98 kg/cm$^2$-G)), to promote the condensation of methanol. The synthesis gas having flowed in the line 10 was subjected to the heat exchange in the preheater 27 with the outlet gas including the reaction product, flowing in the line 12 of the outlet of the reactor 28, and thus preheated to 200° C. As the reactor 28, a reactor having the inner tubes 29 made of a carbon steel was used. In the catalyst layer, the pressure of the fluid was 9.6 MPa-G (98 kg/cm$^2$-G), and the temperature was between 200 and 267° C. The outlet gas including methanol, flowing out from the reactor 28 into the line 12, was cooled in the preheater 27, and then cooled to 45° C. by the condenser 30 to further condense methanol. The molar flow rate of the circulation gas was controlled so as to be equal to the molar flow rate of the make-up gas, and consequently, the molar flow rate of the purge gas based on the molar flow rate of the unreacted gas in the line 13 was 19.4%.

The mass balances are shown in Table 1. The line numbers in Table 1 are the line numbers shown in FIG. 1, and the temperature, the pressure and the material flow rates of the fluid flowing in each of the lines are shown.

TABLE 1

| Line number | Temperature ° C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 467 | 888 | 4312 | 182 | 8 | 7 | 0 | 0 |
| 4 | 142 | 9.9 | 700 | 1333 | 6469 | 273 | 12 | 10 | 0 | 0 |
| 5 | 51 | 9.9 | 197 | 50 | 12435 | 1808 | 84 | 4 | 80 | 3 |
| 6 | 200 | 9.9 | 663 | 938 | 16748 | 1990 | 92 | 10 | 80 | 3 |
| 7 | 230 | 9.8 | 147 | 37 | 13397 | 1990 | 92 | 530 | 1491 | 6 |
| 8 | 45 | 9.6 | 143 | 37 | 13378 | 1982 | 92 | 5 | 83 | 3 |
| 9 | 45 | 9.6 | 4 | 0 | 19 | 8 | 0 | 525 | 1408 | 3 |
| 11 | 200 | 9.6 | 843 | 1370 | 19847 | 2254 | 104 | 14 | 83 | 3 |
| 12 | 231 | 9.6 | 252 | 62 | 15457 | 2254 | 104 | 609 | 1975 | 7 |
| 14 | 45 | 9.4 | 8 | 0 | 24 | 10 | 0 | 604 | 1876 | 3 |
| 15 | 45 | 9.4 | 47 | 12 | 2998 | 436 | 20 | 1 | 19 | 1 |

The highest temperature of the catalyst layer in Example 1 was 262° C. in the inner tubes 24 of the reactor 23, and 267° C. in the inner tubes 29 of the reactor 28, these temperatures falling within an extremely preferable temperature range as the catalyst use temperature range. In this case, the temperature of the pressurized boiling water, a coolant, was 230° C.

The carbon yield in Example 1 is represented by the methanol molar flow rate (the sum of the methanol molar flow rate in the line 9 and the methanol molar flow rate in the line 14) in the crude methanol based on the sum of the CO molar flow rate and the $CO_2$ molar flow rate in the make-up gas (the sum of the CO molar flow rate and the $CO_2$ molar flow rate in the line 3 and the line 4), and was 96.9%.

Comparative Example 1

In Comparative Example 1, the production apparatus shown in FIG. 2 was used. Comparative Example 1 is different from Example 1 in that the first condensation separation step subsequent to the first synthesis step is absent. Specifically, the synthesis gas passing through the reactor 23 and including the produced methanol passed through the preheater 22 from the line 7, was mixed with 60% of the make-up gas taken out into the line 4 of the make-up gas in a line 2, and was supplied to the reactor 28 from the preheater 27 and the line 11. The composition and the total molar flow rate of the raw material gas were set to be the same as in Example 1, and the pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28. Comparative Example 1 is based on the technique of Patent Document 1.

The mass balances are shown in Table 2. The line numbers in Table 2 are the line numbers shown in FIG. 2, and the temperature, the pressure and the material flow rates of the fluid flowing in each of the lines are shown.

The highest temperature of the catalyst layer in Comparative Example 1 was 243° C. in the inner tubes 24 of the reactor 23, and 238° C. in the inner tubes 29 of the reactor 28. In this case, the temperature of the pressurized boiling water, a coolant, was 230° C.

The carbon yield in Comparative Example 1 was 83.5%.

The difference between Example 1 and Comparative Example 1 is whether or not a condensation separation step is present between the two synthesis steps. The results of Example 1 having the condensation separation step were improved in the carbon yield by 13.4% to exhibit a remarkable effect, as compared with the results of Comparative Example 1 having no condensation separation step. Moreover, the reduction of the catalyst amount is also made possible if the effect of the yield improvement is used.

Comparative Example 2

In Comparative Example 2, the production apparatus shown in FIG. 2 was used. Comparative Example 2 is different from Comparative Example 1 in that the circulation ratio was different and the circulation ratio was set to be 3.0. The composition and the total molar flow rate of the raw material gas were set to be the same as in Example 1 and Comparative Example 1, and the pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28. Comparative Example 2 is based on the technique of Patent Document 1.

The mass balances are shown in Table 3. The line numbers in Table 3 are the line numbers shown in FIG. 2, and the temperature, the pressure and the material flow rates of the fluid flowing in each of the lines are shown.

TABLE 2

| Line number | Temperature ° C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 467 | 888 | 4312 | 182 | 8 | 7 | 0 | 0 |
| 4 | 142 | 9.9 | 700 | 1333 | 6469 | 273 | 12 | 10 | 0 | 0 |
| 5 | 50 | 9.9 | 887 | 433 | 11985 | 1264 | 58 | 4 | 79 | 3 |
| 6 | 200 | 9.9 | 1354 | 1321 | 16297 | 1446 | 66 | 10 | 79 | 3 |
| 7 | 233 | 9.8 | 712 | 252 | 12235 | 1446 | 66 | 655 | 1783 | 7 |
| 11 | 200 | 9.7 | 1412 | 1585 | 18703 | 1718 | 78 | 665 | 1783 | 7 |
| 12 | 234 | 9.7 | 1251 | 587 | 16225 | 1718 | 78 | 828 | 2937 | 9 |
| 14 | 45 | 9.5 | 53 | 2 | 35 | 11 | 0 | 823 | 2830 | 5 |
| 15 | 45 | 9.5 | 311 | 152 | 4205 | 443 | 20 | 1 | 28 | 1 |

TABLE 3

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 468 | 892 | 4328 | 182 | 8 | 7 | 0 | 0 |
| 4 | 142 | 9.9 | 703 | 1337 | 6492 | 274 | 12 | 10 | 0 | 0 |
| 5 | 51 | 9.9 | 559 | 186 | 37434 | 5443 | 252 | 12 | 239 | 10 |
| 6 | 200 | 9.9 | 1028 | 1078 | 41762 | 5625 | 260 | 19 | 239 | 10 |
| 7 | 231 | 9.8 | 256 | 57 | 37405 | 5625 | 260 | 795 | 2024 | 13 |
| 11 | 200 | 9.7 | 958 | 1395 | 43896 | 5899 | 273 | 804 | 2024 | 13 |
| 12 | 233 | 9.6 | 618 | 202 | 40488 | 5899 | 273 | 1148 | 3552 | 16 |
| 14 | 45 | 9.4 | 13 | 0 | 42 | 18 | 0 | 1135 | 3294 | 6 |
| 15 | 45 | 9.4 | 45 | 15 | 3011 | 438 | 20 | 1 | 19 | 1 |

The highest temperature of the catalyst layer in Comparative Example 2 was 248° C. in the inner tubes 24 of the reactor 23, and 241° C. in the inner tubes 29 of the reactor 28. In this case, the temperature of the pressurized boiling water, a coolant, was 230° C.

The carbon yield in Comparative Example 2 was 96.9%.

The difference between Comparative Example 1 and Comparative Example 2 is that the circulation ratios were 1.0 and 3.0 in Comparative Examples 1 and 2, respectively, and this difference made the yield of Comparative Example 2 equivalent to the yield in Example 1. The difference between Example 1 and Comparative Example 2 is whether or not a condensation separation step is present between the two synthesis steps, and is in the circulation ratio. The amount of the cooling-treated gas (the amount of the gas cooled in the condenser) is the sum of the gas amounts in the line 7 and the line 12 in Example 1, and is the amount of the gas in the line 12 in Comparative Example 2. The ratio of the amount of the cooling-treated gas of Comparative Example 2 to the amount of the cooling-treated gas in Example 1 is 1.36, and thus Example 1 is reduced in the cooling load as compared with Comparative Example 2. In addition, the amount of the gas treated in the circulator 32 of Example 1 is ⅓ times the amount of the gas treated in the circulator 32 of Comparative Example 2, and thus Example 1 is also reduced in the load of the circulator.

As described above, it has been found that according to the present invention, by drastically reducing the circulation ratio, even a production system performing condensation separation between a plurality of synthesis steps is a system capable of achieving energy reduction while the carbon yield is being maintained. In particular, it has been found that by using the preferable catalyst, namely, the catalyst including copper atoms and zinc atoms in an atomic ratio (copper/zinc) of 2.0 to 3.0 and additionally aluminum atoms, the compatibility between the maintenance of the carbon yield at a high value and the reduction of energy can be achieved more satisfactorily.

Example 2

In Example 2, the production apparatus shown in FIG. 1 was used. The involved conditions were as follows. Specifically, the raw material gas was adjusted to have the same composition as the composition of the raw material gas used in Example 1, and the synthesis of methanol was performed under the condition of the circulation ratio of 1.1. Additionally, 50 mol % of the make-up gas was allowed to flow in the line 3, and the residual make-up gas, namely, 50 mol % of the make-up gas was allowed to flow in the line 4. The amount of the purge gas extracted from the line 15 to outside the system was regulated so as for the circulation ratio to be 1.1. The pressure increased with the compressor 21 and the temperatures in the line 6 and the line 11 were set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 4. The line numbers in Table 4 are the line numbers shown in FIG. 1, and the temperature, the pressure and the material flow rates of the fluid flowing in each of the lines are shown.

TABLE 4

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 582 | 1107 | 5372 | 227 | 10 | 8 | 0 | 0 |
| 4 | 142 | 9.9 | 582 | 1107 | 5372 | 227 | 10 | 8 | 0 | 0 |
| 5 | 55 | 9.9 | 178 | 46 | 13653 | 2006 | 93 | 5 | 88 | 4 |
| 6 | 200 | 9.9 | 759 | 1152 | 19025 | 2233 | 103 | 13 | 88 | 4 |
| 7 | 229 | 9.7 | 209 | 51 | 15169 | 2233 | 103 | 567 | 1734 | 7 |
| 8 | 45 | 9.5 | 203 | 50 | 15148 | 2223 | 103 | 5 | 95 | 4 |
| 9 | 45 | 9.5 | 6 | 0 | 21 | 9 | 0 | 562 | 1639 | 3 |
| 11 | 200 | 9.5 | 784 | 1157 | 20520 | 2450 | 113 | 13 | 95 | 4 |
| 12 | 229 | 9.3 | 222 | 56 | 16631 | 2450 | 113 | 579 | 1752 | 7 |
| 14 | 45 | 9.1 | 6 | 0 | 21 | 9 | 0 | 573 | 1645 | 3 |
| 15 | 45 | 9.1 | 38 | 10 | 2957 | 435 | 20 | 1 | 19 | 1 |

The highest temperature of the catalyst layer in Example 2 was 261° C. in the inner tubes 24 of the reactor 23, and 259° C. in the inner tubes 29 of the reactor 28, these temperatures falling within an extremely preferable temperature range as the catalyst use temperature range. In this case, the temperature of the pressurized boiling water, a coolant, was 230° C.

The carbon yield in Example 2 was 97.3%.

Comparative Example 3

In Comparative Example 3, the production apparatus shown in FIG. 1 was used. The involved conditions were as follows. Specifically, the conditions were such that the molar flow rates of the respective components of the raw material gas and the circulation ratio were the same as in Example 2. This Comparative Example is based on the technique of Patent Document 2, the total amount of the make-up gas in the line 2 was allowed to flow in the line 3. The pressure increased with the compressor 21 and the temperatures in the line 6 and the line 11 were also set to be the same as in Example 2. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 5. The line numbers in Table 5 are the line numbers shown in FIG. 1, and the temperature, the pressure and the material flow rates of the fluid flowing in each of the lines are shown.

tive Example 3, the effect on the degradation of the catalyst in the reactor 23 is inferred to be significant. The ratio between the methanol production amounts of the respective reactors ((methanol production amount in reactor 23)/(methanol production amount in reactor 28)) was 1.0 in Example 2, but was unpreferably as extremely high as 4.3 in Comparative Example 3.

In addition, in a comparison between Example 2 and Comparative Example 3, the total amount of the gas introduced into the condenser 25 and the condenser 30 was 41880 kg-mol/h in Example 2 and 45825 kg-mol/h in Comparative Example 3, showing that the load on the condensers was unpreferably higher in Comparative Example 3.

Example 3

In Example 3, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 0.8.

TABLE 5

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 1163 | 2213 | 10744 | 453 | 21 | 16 | 0 | 0 |
| 4 | | | 0 | 0 | 0 | 0 | 0 | 0 | 0 | 0 |
| 5 | 55 | 9.9 | 64 | 16 | 13735 | 2063 | 96 | 7 | 88 | 4 |
| 6 | 200 | 9.9 | 1227 | 2229 | 24479 | 2516 | 116 | 23 | 88 | 4 |
| 7 | 232 | 9.6 | 550 | 197 | 18384 | 2516 | 116 | 705 | 2786 | 9 |
| 8 | 45 | 9.4 | 529 | 197 | 18349 | 2502 | 116 | 5 | 116 | 5 |
| 9 | 45 | 9.4 | 21 | 1 | 34 | 14 | 0 | 700 | 2670 | 4 |
| 11 | 200 | 9.4 | 529 | 197 | 18349 | 2502 | 116 | 5 | 116 | 5 |
| 12 | 229 | 9.2 | 78 | 19 | 16641 | 2502 | 116 | 457 | 743 | 6 |
| 14 | 45 | 9.1 | 1 | 0 | 8 | 4 | 0 | 449 | 636 | 2 |
| 15 | 45 | 9.1 | 14 | 3 | 2898 | 435 | 20 | 1 | 19 | 1 |

The highest temperature of the catalyst layer in Comparative Example 3 was 269° C. in the inner tubes 24 of the reactor 23, and 238° C. in the inner tubes 29 of the reactor 28. In this case, the temperature of the pressurized boiling water, a coolant, was the same as in Example 2, namely, 230° C.

In the circulation ratio and the carbon yield in Comparative Example 3 were 1.1 and 97.9%, respectively.

The difference between Example 2 and Comparative Example 3 is whether the make-up gas is supplied to both of the first synthesis step and the second synthesis step, or only to the first synthesis step. In Example 2, the methanol production amounts of the reactor 23 and the reactor 28 were 1646 kg-mol/h and 1657 kg-mol/h, respectively; in contrast to this, in Comparative Example 3, these methanol production amounts were 2698 kg-mol/h and 626 kg-mol/h, respectively, leading to a result that the load on the reactor 23 was steeply increased, and the catalyst in the reactor 28 was not effectively used. On the basis of these results, in Compara- Additionally, 40 mol % of the make-up gas was allowed to flow in the line 3, and the residual make-up gas, namely, 60 mol % of the make-up gas was allowed to flow in the line 4. The outlet gas from the first synthesis step was cooled to 80° C. with the condenser 25 to promote the condensation of methanol. The amount of the purge gas extracted from the line 15 to outside the system was regulated so as for the circulation ratio to be 0.8. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 6. The line numbers in Table 6 are the line numbers shown in FIG. 1, and the temperature, the pressure and the material flow rates of the fluid flowing in each of the lines are shown.

TABLE 6

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 475 | 904 | 4389 | 185 | 8 | 7 | 0 | 0 |
| 4 | 142 | 9.9 | 713 | 1356 | 6584 | 278 | 13 | 10 | 0 | 0 |
| 5 | 51 | 9.9 | 269 | 81 | 10045 | 1407 | 64 | 3 | 65 | 3 |

TABLE 6-continued

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 6 | 200 | 9.9 | 744 | 985 | 14434 | 1592 | 73 | 10 | 65 | 3 |
| 7 | 238 | 9.8 | 220 | 58 | 11006 | 1592 | 73 | 537 | 1511 | 6 |
| 8 | 80 | 9.6 | 216 | 58 | 10987 | 1589 | 73 | 20 | 279 | 4 |
| 9 | 80 | 9.6 | 4 | 0 | 19 | 2 | 0 | 517 | 1232 | 2 |
| 11 | 200 | 9.6 | 929 | 1414 | 17571 | 1867 | 85 | 30 | 279 | 4 |
| 12 | 239 | 9.6 | 369 | 108 | 13280 | 1867 | 85 | 593 | 2137 | 8 |
| 14 | 45 | 9.4 | 14 | 0 | 26 | 11 | 0 | 589 | 2052 | 4 |
| 15 | 45 | 9.4 | 86 | 26 | 3209 | 449 | 21 | 1 | 21 | 1 |

In Example 3, the temperature of the pressurized boiling water, a coolant, was 238° C. In this case, the highest temperature of the catalyst layer was 262° C. in the inner tubes 24 of the reactor 23, and 261° C. in the inner tubes 29 of the reactor 28, and the carbon yield was 95.2%.

Example 4

In Example 4, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 0.6.

In the line 4, 50 mol % of the make-up gas was allowed to flow in the line 3, and the residual make-up gas, namely, 50 mol % of the make-up gas was allowed to flow. The outlet gas from the first synthesis step was cooled to 30° C. with the condenser 25 to promote the condensation of methanol. The amount of the purge gas extracted from the line 15 to outside the system was regulated so as for the circulation ratio to be 0.6. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 7. The line numbers in Table 7 are the line numbers shown in FIG. 1, and the temperature, the pressure and the material flow rates of the fluid flowing in each of the lines are shown.

The highest temperature of the catalyst layer in Example 4 was 260° C. in the inner tubes 24 of the reactor 23, and 259° C. in the inner tubes 29 of the reactor 28, and the carbon yield was 94.5%.

Example 5

In Example 5, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.6.

Additionally, 70 mol % of the make-up gas was allowed to flow in the line 3, and the residual make-up gas, namely, 30 mol % of the make-up gas was allowed to flow in the line 4. The outlet gas from the first synthesis step was cooled to 20° C. with the condenser 25 to promote the condensation of methanol. The amount of the purge gas extracted from the line 15 to outside the system was regulated so as for the circulation ratio to be 1.6. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 8. The line numbers in Table 8 are the line numbers shown in FIG. 1, and the temperature, the pressure and the material flow rates of the fluid flowing in each of the lines are shown.

TABLE 7

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 598 | 1139 | 5529 | 233 | 11 | 8 | 0 | 0 |
| 4 | 142 | 9.9 | 598 | 1139 | 5529 | 233 | 11 | 8 | 0 | 0 |
| 5 | 51 | 9.9 | 227 | 58 | 7610 | 1026 | 48 | 3 | 49 | 2 |
| 6 | 200 | 9.9 | 825 | 1197 | 13139 | 1259 | 58 | 11 | 49 | 2 |
| 7 | 239 | 9.8 | 318 | 76 | 9377 | 1259 | 58 | 521 | 1670 | 5 |
| 8 | 30 | 9.6 | 299 | 76 | 9358 | 1249 | 58 | 1 | 29 | 2 |
| 9 | 30 | 9.6 | 19 | 0 | 20 | 11 | 0 | 519 | 1641 | 3 |
| 11 | 200 | 9.6 | 898 | 1215 | 14887 | 1482 | 69 | 10 | 29 | 2 |
| 12 | 239 | 9.6 | 338 | 84 | 10944 | 1482 | 69 | 573 | 1714 | 5 |
| 14 | 45 | 9.4 | 13 | 0 | 21 | 8 | 0 | 569 | 1644 | 3 |
| 15 | 45 | 9.4 | 99 | 25 | 3314 | 447 | 21 | 1 | 21 | 1 |

TABLE 8

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 806 | 1534 | 7444 | 314 | 14 | 11 | 0 | 0 |
| 4 | 142 | 9.9 | 345 | 657 | 3190 | 135 | 6 | 5 | 0 | 0 |
| 5 | 52 | 9.9 | 74 | 32 | 19798 | 2958 | 139 | 8 | 126 | 4 |
| 6 | 200 | 9.9 | 880 | 1565 | 27242 | 3272 | 153 | 19 | 126 | 4 |
| 7 | 236 | 9.8 | 236 | 77 | 22335 | 3272 | 153 | 667 | 2249 | 8 |
| 8 | 20 | 9.6 | 225 | 77 | 22310 | 3254 | 153 | 2 | 41 | 3 |
| 9 | 20 | 9.6 | 10 | 0 | 25 | 19 | 0 | 665 | 2208 | 5 |
| 11 | 200 | 9.6 | 571 | 735 | 25500 | 3388 | 159 | 6 | 41 | 3 |
| 12 | 235 | 9.5 | 85 | 36 | 22648 | 3388 | 159 | 494 | 1220 | 6 |
| 14 | 45 | 9.3 | 1 | 0 | 14 | 6 | 0 | 485 | 1076 | 2 |
| 15 | 45 | 9.3 | 11 | 5 | 2836 | 424 | 20 | 1 | 18 | 1 |

In Example 5, the temperature of the pressurized boiling water, a coolant, was 235° C. In this case, the highest temperature of the catalyst layer was 263° C. in the inner tubes 24 of the reactor 23, and 252° C. in the inner tubes 29 of the reactor 28, and the carbon yield was 98.3%.

Example 6

In Example 6, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.2.

Additionally, 40 mol % of the make-up gas was allowed to flow in the line 3, and the residual make-up gas, namely, 60 mol % of the make-up gas was allowed to flow in the line 4. The outlet gas from the first synthesis step was cooled to 80° C. with the condenser 25 to promote the condensation of methanol. The amount of the purge gas extracted from the line 15 to outside the system was regulated so as for the circulation ratio to be 1.2. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 9. The line numbers in Table 9 are the line numbers shown in FIG. 1, and the temperature, the pressure and the material flow rates of the fluid flowing in each of the lines are shown.

In Example 6, the temperature of the pressurized boiling water, a coolant, was 240° C. In this case, the highest temperature of the catalyst layer was 267° C. in the inner tubes 24 of the reactor 23, and 266° C. in the inner tubes 29 of the reactor 28, and the carbon yield was 96.9%.

Example 7

In Example 7, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.0.

Additionally, 40 mol % of the make-up gas was allowed to flow in the line 3, and the residual make-up gas, namely, 60 mol % of the make-up gas was allowed to flow in the line 4. The outlet gas from the first synthesis step was cooled to 80° C. with the condenser 25 to promote the condensation of methanol. The amount of the purge gas extracted from the line 15 to outside the system was regulated so as for the circulation ratio to be 1.0. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 10. The line numbers in Table 10 are the line numbers shown in FIG. 1, and the temperature, the pressure and the material flow rates of the fluid flowing in each of the lines are shown.

TABLE 9

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurtty |
| 3 | 142 | 9.9 | 467 | 889 | 4314 | 182 | 8 | 7 | 0 | 0 |
| 4 | 142 | 9.9 | 700 | 1333 | 6470 | 273 | 12 | 10 | 0 | 0 |
| 5 | 51 | 9.9 | 222 | 85 | 14894 | 2191 | 101 | 4 | 96 | 5 |
| 6 | 200 | 9.9 | 689 | 973 | 19208 | 2373 | 109 | 11 | 96 | 5 |
| 7 | 240 | 9.8 | 152 | 57 | 15765 | 2373 | 109 | 551 | 1543 | 7 |
| 8 | 80 | 9.6 | 151 | 57 | 15747 | 2370 | 109 | 30 | 398 | 6 |
| 9 | 80 | 9.6 | 2 | 0 | 18 | 2 | 0 | 521 | 1145 | 1 |
| 11 | 200 | 9.6 | 851 | 1390 | 22218 | 2643 | 121 | 40 | 398 | 6 |
| 12 | 240 | 9.6 | 275 | 102 | 17915 | 2643 | 121 | 619 | 2255 | 10 |
| 14 | 45 | 9.4 | 8 | 0 | 27 | 12 | 0 | 614 | 2140 | 4 |
| 15 | 45 | 9.4 | 45 | 17 | 2993 | 440 | 20 | 1 | 19 | 1 |

TABLE 10

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 468 | 892 | 4328 | 182 | 8 | 7 | 0 | 0 |
| 4 | 142 | 9.9 | 703 | 1337 | 6492 | 274 | 12 | 10 | 0 | 0 |
| 5 | 51 | 9.9 | 229 | 60 | 12442 | 1810 | 83 | 4 | 80 | 4 |
| 6 | 200 | 9.9 | 697 | 952 | 16770 | 1993 | 91 | 10 | 80 | 4 |
| 7 | 230 | 9.8 | 162 | 39 | 13341 | 1993 | 91 | 548 | 1522 | 7 |
| 8 | 80 | 9.6 | 160 | 39 | 13322 | 1990 | 91 | 25 | 337 | 5 |
| 9 | 80 | 9.6 | 2 | 0 | 18 | 2 | 0 | 523 | 1185 | 2 |
| 11 | 200 | 9.6 | 863 | 1376 | 19814 | 2264 | 104 | 35 | 337 | 5 |
| 12 | 231 | 9.6 | 295 | 75 | 15507 | 2264 | 104 | 607 | 2199 | 9 |
| 14 | 45 | 9.4 | 10 | 0 | 27 | 12 | 0 | 602 | 2099 | 4 |
| 15 | 45 | 9.4 | 56 | 15 | 3038 | 442 | 20 | 1 | 20 | 1 |

In Example 7, the temperature of the pressurized boiling water, a coolant, was 230° C. In this case, the highest temperature of the catalyst layer was 261° C. in the inner tubes 24 of the reactor 23, and 261° C. in the inner tubes 29 of the reactor 28, and the carbon yield was 96.6%.

Example 8

In Example 8, the production apparatus shown in FIG. 3 was used. The involved conditions were as follows. Specifically, the raw material gas was regulated to have the same composition as the composition of the raw material gas used in Example 1, and the synthesis of methanol was performed under the condition of the circulation ratio of 1.0.

Additionally, 60 mol % of the make-up gas was allowed to flow in the line 3, and the residual make-up gas, namely, 40 mol % of the make-up gas was allowed to flow in the line 4. The outlet gas from the first synthesis step was cooled to 60° C. with the condenser 25 to promote the condensation of methanol. The amount of the purge gas extracted from the line 15 to outside the system was regulated so as for the circulation ratio to be 0.8. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst B was filled in the reactor 23 and the reactor 28.

The difference from the production apparatus of FIG. 1 is in that the steam drum of the boiler water used for cooling the catalyst layer was provided for each of the reactors. The temperature of the pressurized boiling water was 240° C. on the side of the reactor 23 and 244° C. on the side of the reactor 28.

The mass balances are shown in Table 11. The line numbers in Table 11 are the line numbers shown in FIG. 3, and the temperature, the pressure and the material flow rates of the fluid flowing in each of the lines are shown.

The highest temperature of the catalyst layer in Example 8 was 264° C. in the inner tubes 24 of the reactor 23, and 265° C. in the inner tubes 29 of the reactor 28, and the carbon yield was 96.9%.

By regulating the pressure of the pressurized boiling water as a coolant for each of the reactors, the energy level of the obtained steam was able to be made high under the condition that the highest temperature of the catalyst layer was made to fall within a preferable temperature range. Additionally, the methanol production amounts of the respective reactors were different from each other, and by increasing the pressure of the pressurized boiling water of the reactor 28 low in the methanol production amount, the methanol synthesis reaction was able to be promoted and the carbon yield was able to be improved.

Example 9

In Example 9, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.5.

Additionally, 30 mol % of the make-up gas was allowed to flow in the line 3, and the residual make-up gas, namely, 70 mol % of the make-up gas was allowed to flow in the line 4. The outlet gas from the first synthesis step was cooled to 100° C. with the condenser 25 to promote the condensation of methanol. The amount of the purge gas extracted from the line 15 to outside the system was regulated so as for the circulation ratio to be 1.5. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst B was filled in the reactor 23 and the reactor 28.

TABLE 11

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 701 | 1334 | 6474 | 273 | 12 | 10 | 0 | 0 |
| 4 | 142 | 9.9 | 467 | 889 | 4316 | 182 | 8 | 7 | 0 | 0 |
| 5 | 51 | 9.9 | 180 | 70 | 12431 | 1820 | 84 | 4 | 80 | 4 |
| 6 | 200 | 9.8 | 881 | 1404 | 18905 | 2093 | 96 | 14 | 80 | 4 |
| 7 | 241 | 9.8 | 316 | 102 | 14609 | 2093 | 96 | 582 | 1938 | 7 |
| 8 | 60 | 9.6 | 308 | 102 | 14584 | 2086 | 96 | 10 | 174 | 5 |
| 9 | 60 | 9.6 | 8 | 0 | 25 | 7 | 0 | 573 | 1764 | 3 |
| 11 | 200 | 9.5 | 776 | 991 | 18900 | 2267 | 104 | 16 | 174 | 5 |
| 12 | 244 | 9.5 | 229 | 87 | 15452 | 2267 | 104 | 565 | 1619 | 8 |
| 14 | 45 | 9.3 | 6 | 0 | 19 | 8 | 0 | 560 | 1520 | 3 |
| 15 | 45 | 9.3 | 43 | 17 | 3002 | 439 | 20 | 1 | 19 | 1 |

The mass balances are shown in Table 12. The line numbers in Table 12 are the line numbers shown in FIG. 1, and the temperature, the pressure and the material flow rates of the fluid flowing in each of the lines are shown.

TABLE 12

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 354 | 673 | 3268 | 138 | 6 | 5 | 0 | 0 |
| 4 | 142 | 9.9 | 825 | 1571 | 7626 | 321 | 15 | 11 | 0 | 0 |
| 5 | 52 | 9.9 | 357 | 177 | 18748 | 2684 | 123 | 5 | 121 | 6 |
| 6 | 200 | 9.9 | 710 | 850 | 22016 | 2821 | 130 | 10 | 121 | 6 |
| 7 | 245 | 9.8 | 150 | 69 | 18770 | 2821 | 130 | 574 | 1458 | 8 |
| 8 | 100 | 9.6 | 149 | 69 | 18761 | 2821 | 130 | 107 | 936 | 8 |
| 9 | 100 | 9.6 | 1 | 0 | 9 | 0 | 0 | 466 | 522 | 1 |
| 11 | 200 | 9.6 | 974 | 1640 | 26387 | 3143 | 144 | 119 | 936 | 8 |
| 12 | 246 | 9.5 | 430 | 207 | 21887 | 3143 | 144 | 667 | 2905 | 12 |
| 14 | 45 | 9.3 | 14 | 1 | 35 | 15 | 0 | 662 | 2764 | 5 |
| 15 | 45 | 9.3 | 59 | 29 | 3104 | 444 | 20 | 1 | 20 | 1 |

In Example 9, the temperature of the pressurized boiling water, a coolant, was 245° C. In this case, the highest temperature of the catalyst layer was 265° C. in the inner tubes 24 of the reactor 23, and 266° C. in the inner tubes 29 of the reactor 28, and the carbon yield was 96.0%.

Example 10

In Example 10, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.7.

Additionally, 40 mol % of the make-up gas was allowed to flow in the line 3, and the residual make-up gas, namely, 60 mol % of the make-up gas was allowed to flow in the line 4. The outlet gas from the first synthesis step was cooled to 70° C. with the condenser 25 to promote the condensation of methanol. The amount of the purge gas extracted from the line 15 to outside the system was regulated so as for the circulation ratio to be 1.7. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst A was filled in the reactor 23 and the reactor 28.

The mass balances are shown in Table 13. The line numbers in Table 13 are the line numbers shown in FIG. 1, and the temperature, the pressure and the material flow rates of the fluid flowing in each of the lines are shown.

In Example 10, the temperature of the pressurized boiling water, a coolant, was 250° C. In this case, the highest temperature of the catalyst layer was 267° C. in the inner tubes 24 of the reactor 23, and 267° C. in the inner tubes 29 of the reactor 28, and the carbon yield was 96.1%.

Example 11

In Example 11, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.2.

Additionally, 40 mol % of the make-up gas was allowed to flow in the line 3, and the residual make-up gas, namely, 60 mol % of the make-up gas was allowed to flow in the line 4. The outlet gas from the first synthesis step was cooled to 80° C. with the condenser 25 to promote the condensation of methanol. The amount of the purge gas extracted from the line 15 to outside the system was regulated so as for the circulation ratio to be 1.2. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst A was filled in the reactor 23 and the reactor 28.

The mass balances are shown in Table 14. The line numbers in Table 14 are the line numbers shown in FIG. 1, and the temperature, the pressure and the material flow rates of the fluid flowing in each of the lines are shown.

TABLE 13

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 471 | 896 | 4351 | 183 | 8 | 7 | 0 | 0 |
| 4 | 142 | 9.9 | 706 | 1345 | 6526 | 275 | 12 | 10 | 0 | 0 |
| 5 | 52 | 9.9 | 362 | 247 | 21198 | 3048 | 140 | 6 | 137 | 6 |
| 6 | 200 | 9.9 | 833 | 1143 | 25549 | 3231 | 148 | 13 | 137 | 6 |
| 7 | 252 | 9.8 | 274 | 156 | 21898 | 3231 | 148 | 575 | 1677 | 9 |
| 8 | 70 | 9.6 | 271 | 156 | 21879 | 3227 | 148 | 26 | 384 | 8 |
| 9 | 70 | 9.6 | 3 | 0 | 19 | 4 | 0 | 549 | 1293 | 2 |
| 11 | 200 | 9.6 | 978 | 1500 | 28405 | 3502 | 161 | 36 | 384 | 8 |
| 12 | 253 | 9.5 | 424 | 283 | 24310 | 3502 | 161 | 593 | 2148 | 11 |
| 14 | 45 | 9.3 | 9 | 1 | 25 | 11 | 0 | 586 | 1991 | 4 |
| 15 | 45 | 9.3 | 53 | 36 | 3086 | 444 | 20 | 1 | 20 | 1 |

TABLE 14

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 484 | 922 | 4475 | 189 | 9 | 7 | 0 | 0 |
| 4 | 142 | 9.9 | 727 | 1383 | 6712 | 283 | 13 | 10 | 0 | 0 |
| 5 | 51 | 9.9 | 479 | 294 | 15235 | 2044 | 94 | 5 | 99 | 5 |
| 6 | 200 | 9.9 | 963 | 1216 | 19709 | 2233 | 102 | 11 | 99 | 5 |
| 7 | 252 | 9.8 | 410 | 189 | 15996 | 2233 | 102 | 567 | 1673 | 8 |
| 8 | 80 | 9.6 | 405 | 189 | 15977 | 2230 | 102 | 30 | 409 | 6 |
| 9 | 80 | 9.6 | 5 | 0 | 19 | 2 | 0 | 538 | 1264 | 2 |
| 11 | 200 | 9.6 | 1132 | 1571 | 22689 | 2513 | 115 | 40 | 409 | 6 |
| 12 | 253 | 9.6 | 602 | 361 | 18681 | 2513 | 115 | 572 | 2141 | 10 |
| 14 | 45 | 9.4 | 16 | 1 | 25 | 10 | 0 | 567 | 2019 | 4 |
| 15 | 45 | 9.4 | 107 | 66 | 3421 | 459 | 21 | 1 | 22 | 1 |

In Example 11, the temperature of the pressurized boiling water, a coolant, was 250° C. In this case, the highest temperature of the catalyst layer was 267° C. in the inner tubes 24 of the reactor 23, and 266° C. in the inner tubes 29 of the reactor 28, and the carbon yield was 93.4%.

Example 12

In Example 12, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.2.

Additionally, 24 mol % of the make-up gas was allowed to flow in the line 3, and the residual make-up gas, namely, 76 mol % of the make-up gas was allowed to flow in the line 4. The outlet gas from the first synthesis step was cooled to 80° C. with the condenser 25 to promote the condensation of methanol. The amount of the purge gas extracted from the line 15 to outside the system was regulated so as for the circulation ratio to be 1.2. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 15. The line numbers in Table 15 are the line numbers shown in FIG. 1, and the temperature, the pressure and the material flow rates of the fluid flowing in each of the lines are shown.

In Example 12, the temperature of the pressurized boiling water, a coolant, was 240° C. In this case, the highest temperature of the catalyst layer was 261° C. in the inner tubes 24 of the reactor 23, and 270° C. in the inner tubes 29 of the reactor 28, and the carbon yield was 96.1%.

Example 13

In Example 13, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.4.

Additionally, 50 mol % of the make-up gas was allowed to flow in the line 3, and the residual make-up gas, namely, 50 mol % of the make-up gas was allowed to flow in the line 4. The outlet gas from the first synthesis step was cooled to 50° C. with the condenser 25 to promote the condensation of methanol. The amount of the purge gas extracted from the line 15 to outside the system was regulated so as for the circulation ratio to be 1.4. The pressure increased with the compressor 21 and the temperatures in the line 6 and the line 11 were also set to be the same as in Example 1. Additionally, a stainless steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 16. The line numbers in Table 16 are the line numbers shown in FIG. 1, and the temperature, the pressure and the material flow rates of the fluid flowing in each of the lines are shown.

TABLE 15

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 282 | 538 | 2609 | 110 | 5 | 4 | 0 | 0 |
| 4 | 142 | 9.9 | 894 | 1702 | 8262 | 348 | 16 | 12 | 0 | 0 |
| 5 | 51 | 9.9 | 300 | 110 | 14978 | 2147 | 99 | 4 | 96 | 4 |
| 6 | 200 | 9.9 | 583 | 648 | 17587 | 2257 | 104 | 8 | 96 | 4 |
| 7 | 240 | 9.8 | 102 | 41 | 14931 | 2257 | 104 | 492 | 1179 | 7 |
| 8 | 80 | 9.6 | 101 | 41 | 14919 | 2255 | 104 | 32 | 376 | 5 |
| 9 | 80 | 9.6 | 1 | 0 | 12 | 2 | 0 | 459 | 803 | 1 |
| 11 | 200 | 9.6 | 995 | 1743 | 23180 | 2603 | 119 | 45 | 376 | 5 |
| 12 | 241 | 9.6 | 375 | 133 | 18101 | 2603 | 119 | 668 | 2597 | 10 |
| 14 | 45 | 9.4 | 13 | 0 | 31 | 13 | 0 | 663 | 2481 | 5 |
| 15 | 45 | 9.4 | 62 | 23 | 3092 | 443 | 20 | 1 | 20 | 1 |

TABLE 16

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 578 | 1101 | 5343 | 225 | 10 | 8 | 0 | 0 |
| 4 | 142 | 9.9 | 578 | 1101 | 5343 | 225 | 10 | 8 | 0 | 0 |
| 5 | 51 | 9.9 | 166 | 40 | 17309 | 2590 | 120 | 6 | 111 | 5 |
| 6 | 200 | 9.9 | 744 | 1141 | 22653 | 2815 | 130 | 14 | 111 | 5 |
| 7 | 226 | 9.8 | 183 | 41 | 18771 | 2815 | 130 | 578 | 1764 | 8 |
| 8 | 50 | 9.6 | 180 | 41 | 18749 | 2806 | 130 | 8 | 146 | 5 |
| 9 | 50 | 9.6 | 4 | 0 | 22 | 9 | 0 | 570 | 1619 | 3 |
| 11 | 200 | 9.6 | 758 | 1142 | 24093 | 3031 | 140 | 16 | 146 | 5 |
| 12 | 226 | 9.6 | 198 | 46 | 20222 | 3031 | 140 | 579 | 1795 | 8 |
| 14 | 45 | 9.4 | 4 | 0 | 21 | 10 | 0 | 573 | 1665 | 3 |
| 15 | 45 | 9.4 | 28 | 7 | 2891 | 433 | 20 | 1 | 19 | 1 |

In Example 13, the temperature of the pressurized boiling water, a coolant, was 225° C. In this case, the highest temperature of the catalyst layer was 265° C. in the inner tubes 24 of the reactor 23, and 261° C. in the inner tubes 29 of the reactor 28, and the carbon yield was 97.8%.

Example 14

In Example 14, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.4.

Additionally, 50 mol % of the make-up gas was allowed to flow in the line 3, and the residual make-up gas, namely, 50 mol % of the make-up gas was allowed to flow in the line 4. The outlet gas from the first synthesis step was cooled to 50° C. with the condenser 25 to promote the condensation of methanol. The amount of the purge gas extracted from the line 15 to outside the system was regulated so as for the circulation ratio to be 1.4. The pressure increased with the compressor 21 and the temperatures in the line 6 and the line 11 were also set to be the same as in Example 1. A stainless steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 17. The line numbers in Table 17 are the line numbers shown in FIG. 1, and the temperature, the pressure and the material flow rates of the fluid flowing in each of the lines are shown.

In Example 14, the temperature of the pressurized boiling water, a coolant, was 217° C. In this case, the highest temperature of the catalyst layer was 237° C. in the inner tubes 24 of the reactor 23, and 235° C. in the inner tubes 29 of the reactor 28, and the carbon yield was 95.3%.

Example 15

In Example 15, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 0.9.

Additionally, 50 mol % of the make-up gas was allowed to flow in the line 3, and the residual make-up gas, namely, 50 mol % of the make-up gas was allowed to flow in the line 4. The outlet gas from the first synthesis step was cooled to 45° C. with the condenser 25 to promote the condensation of methanol. The amount of the purge gas extracted from the line 15 to outside the system was regulated so as for the circulation ratio to be 0.9. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst C was filled in the reactor 23 and the reactor 28.

The mass balances are shown in Table 18. The line numbers in Table 18 are the line numbers shown in FIG. 1, and the temperature, the pressure and the material flow rates of the fluid flowing in each of the lines are shown.

TABLE 17

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 594 | 1130 | 5485 | 231 | 10 | 8 | 0 | 0 |
| 4 | 142 | 9.9 | 594 | 1130 | 5485 | 231 | 10 | 8 | 0 | 0 |
| 5 | 52 | 9.9 | 413 | 186 | 17596 | 2452 | 113 | 6 | 114 | 5 |
| 6 | 200 | 9.9 | 1007 | 1316 | 23081 | 2683 | 124 | 14 | 114 | 5 |
| 7 | 222 | 9.8 | 466 | 192 | 19212 | 2683 | 124 | 558 | 1771 | 8 |
| 8 | 50 | 9.6 | 457 | 191 | 19190 | 2675 | 123 | 8 | 151 | 5 |
| 9 | 50 | 9.6 | 10 | 0 | 22 | 8 | 0 | 550 | 1621 | 3 |
| 11 | 200 | 9.6 | 1051 | 1321 | 24675 | 2906 | 134 | 16 | 151 | 5 |
| 12 | 222 | 9.6 | 499 | 220 | 20816 | 2906 | 134 | 571 | 1798 | 9 |
| 14 | 45 | 9.4 | 10 | 0 | 21 | 9 | 0 | 564 | 1663 | 3 |
| 15 | 45 | 9.4 | 75 | 34 | 3199 | 446 | 21 | 1 | 21 | 1 |

TABLE 18

| Line number | Temperature ° C. | Pressure MPa-G | Flow rate kg-mol/h | | | | | | | |
|---|---|---|---|---|---|---|---|---|---|---|
| | | | CO$_2$ | CO | H$_2$ | CH$_4$ | N$_2$ | H$_2$O | CH$_3$OH | Impurity |
| 3 | 142 | 9.9 | 585 | 1113 | 5401 | 228 | 10 | 8 | 0 | 0 |
| 4 | 142 | 9.9 | 585 | 1113 | 5401 | 228 | 10 | 8 | 0 | 0 |
| 5 | 51 | 9.9 | 179 | 56 | 11209 | 1622 | 75 | 4 | 72 | 3 |
| 6 | 200 | 9.9 | 764 | 1168 | 16610 | 1850 | 85 | 12 | 72 | 3 |
| 7 | 238 | 9.8 | 222 | 65 | 12779 | 1850 | 85 | 556 | 1710 | 6 |
| 8 | 45 | 9.6 | 215 | 64 | 12758 | 1841 | 85 | 4 | 80 | 3 |
| 9 | 45 | 9.6 | 8 | 0 | 21 | 9 | 0 | 552 | 1630 | 3 |
| 11 | 200 | 9.6 | 799 | 1177 | 18158 | 2069 | 96 | 12 | 80 | 3 |
| 12 | 238 | 9.6 | 234 | 71 | 14250 | 2069 | 96 | 581 | 1745 | 7 |
| 14 | 45 | 9.4 | 7 | 0 | 21 | 9 | 0 | 576 | 1654 | 3 |
| 15 | 45 | 9.4 | 48 | 15 | 3020 | 437 | 20 | 1 | 19 | 1 |

In Example 15, the temperature of the pressurized boiling water, a coolant, was 238° C. In this case, the highest temperature of the catalyst layer was 267° C. in the inner tubes 24 of the reactor 23, and 264° C. in the inner tubes 29 of the reactor 28, and the carbon yield was 96.7%.

Comparative Example 4

In Comparative Example 4, the production apparatus shown in FIG. 4 was used. The involved conditions were as follows. Specifically, the molar flow rate of the raw material gas was set to be the same as in Example 15, and the synthesis of methanol was performed under the condition of the circulation ratio of 0.9.

In this case, the circulation ratio is defined by the molar flow rate of the circulation gas based on the molar flow rate of the make-up gas, and the molar flow rate of the circulation gas is the sum of the molar flow rates of a line 16*a* and a line 16*b*.

The synthesis process in Comparative Example 4 includes two synthesis loops, and accordingly the circulation ratio can be defined for each of these synthesis loops. Specifically, such circulation ratios are the circulation ratio a defined by the ratio of the molar flow rate of a fraction of the circulation gas flowing in the line 16*a* to the molar flow rate of a fraction of the make-up gas flowing in the line 3*a*, and the circulation ratio b defined by the ratio of the molar flow rate of a fraction of the circulation gas flowing in the line 16*b* to the molar flow rate of a fraction of the make-up gas flowing in the line 3*b*. The circulation ratios (circulation ratios a and b) in these respective synthesis loops were also set to be the same as the circulation ratio of 0.9 in the whole synthesis process.

The synthesis raw material gas including CO, CO$_2$ and H$_2$, produced by steam-reforming reaction was introduced into the system from the line 1, and was increased in pressure to a pressure of 9.9 MPa-G (101 kg/cm$^2$-G) with the compressor 21. Then, 50 mol % of the synthesis raw material gas (make-up gas) increased in pressure was allowed to flow in the line 3*a*, mixed with the circulation gas from a line 5*a*, and then supplied to the preheater 22*a*. The mixed synthesis gas was subjected to the heat exchange in the preheater 22*a* with the outlet gas including the reaction product flowing in the line 7*a* from the reactor 23*a*, thus preheated to 200° C., and supplied to the reactor 23*a* from the line 6*a*. The residual make-up gas, namely, 50 mol % of the make-up gas was allowed to flow in the line 3*b*.

The reactor 23*a* had the inner tubes 24*a* made of a carbon steel, and the methanol synthesis catalyst C including copper and zinc as the essential components was filled in the inner tubes 24*a* to form the catalyst layer. Methanol was synthesized in the process allowing the synthesis gas supplied from the line 6*a* into the reactor 23*a* to pass through the catalyst layer in the inner tubes 24*a*. In the catalyst layer, the pressure of the fluid was 9.8 to 9.9 MPa-G (100 to 101 kg/cm$^2$-G), and the temperature was between 200 and 254° C.

The outlet gas including methanol, flowing out from the reactor 23*a* into the line 7*a*, was cooled in the preheater 22*a*, then supplied to the condenser 25*a* and cooled to 45° C. to further condense methanol. Of the fluid including the condensed methanol, the condensed fraction was extracted as crude methanol from the line 9*a* to outside the system in the gas-liquid separator 26*a*, and the vapor phase fraction was allowed to flow in the line 8*a*. Of the unreacted gas flowing in the line 8*a*, the unreacted gas of an amount to give a predetermined circulation ratio was recycled as the circulation gas from the line 16*a* through a circulator 32*a* and then from the line 5*a* into the reactor 23*a*, and the residual unreacted gas was extracted as the purge gas from a line 15*a* and from the synthesis loop to outside the system in order to remove the inert component accumulating in the synthesis loop. The circulation ratio in the synthesis loop is the molar flow rate of the gas flowing in the line 16*a* based on the molar flow rate of the gas flowing in the line 3*a*, and was set to be 0.9.

The fraction of the make-up gas, allowed to flow in the line 3*b*, namely, 50 mol % of the make-up gas was mixed with the circulation gas from a line 5*b*, and then supplied to the preheater 22*b*. The mixture of the make-up gas and the circulation gas was subjected to the heat exchange in the preheater 22*b* with the outlet gas including the reaction product flowing in the line 7*b* of the outlet of the reactor 23*b*, thus preheated to 200° C., and supplied to the reactor 23*b* from the line 6*b*. The reactor 23*b* had the inner tubes 24*b* made of a carbon steel, and the methanol synthesis catalyst C including copper and zinc as the essential components was filled in the inner tubes 24*b* to form the catalyst layer. Methanol was synthesized in the process allowing the synthesis gas supplied from the line 6*b* into the reactor 23*b* to pass through the catalyst layer in the inner tubes 24*b*.

The outlet gas including methanol, flowing out from the reactor 23*b* into the line 7*b*, was cooled in the preheater 22*b*, then supplied to the condenser 25*b* and cooled to 45° C. to further condense methanol. Of the fluid including the condensed methanol, the condensed fraction was extracted as crude methanol from the line 9*b* to outside the system in the gas-liquid separator 26*b*, and the vapor phase fraction was allowed to flow in the line 8*b*. Of the unreacted gas flowing in the line 8*b*, the unreacted gas of an amount to give a predetermined circulation ratio was recycled as the circulation gas from the line 16*b* through a circulator 32*b* and then from the line 5b into the reactor 23b. On the other hand, the residual unreacted gas was extracted as the purge gas from a line 15b and from the synthesis loop to outside the system in order to remove the inert component accumulating in the synthesis loop. The circulation ratio in the synthesis loop is the molar flow rate of the gas flowing in the line 16b based on the molar flow rate of the gas flowing in the line 3b, and was set to be 0.9.

The cooling operations of the catalyst layers in the reactors 23a and 23b were performed in the process in which the boiler waters from the steam drums 33a and 33b were introduced from the lines 43a and 43b into the reactors 23a and 23b, respectively, these boiler waters were used as the pressurized boiling waters, and the fluids including the produced steams were collected from the lines 44a and 44b in the steam drums 33a and 33b, respectively. The steams produced by the heats of reaction were taken out from the steam drums 33a and 33b to the lines 42a and 42b, respectively, and the amounts of water to compensate the amounts of the steams were supplied from the lines 41a and 41b to the respective steam drums. The steam taken out from the lines 42a and 42b can be used as the raw material steam necessary for the steam-reforming reaction in the production of the raw material gas from natural gas.

The mass balances are shown in Table 19. The line numbers in Table 19 are the line numbers shown in FIG. 4, and the temperature, the pressure and the material flow rates of the fluid flowing in each of the lines are shown.

TABLE 19

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3a | 142 | 9.9 | 585 | 1113 | 5401 | 228 | 10 | 8 | 0 | 0 |
| 3b | 142 | 9.9 | 585 | 1113 | 5401 | 228 | 10 | 8 | 0 | 0 |
| 5a | 48 | 9.9 | 305 | 75 | 5496 | 665 | 31 | 2 | 35 | 1 |
| 5b | 48 | 9.9 | 305 | 75 | 5496 | 665 | 31 | 2 | 35 | 1 |
| 6a | 200 | 9.9 | 890 | 1188 | 10897 | 892 | 41 | 10 | 35 | 1 |
| 7a | 239 | 9.8 | 429 | 101 | 7340 | 892 | 41 | 474 | 1577 | 4 |
| 6b | 200 | 9.9 | 890 | 1188 | 10897 | 892 | 41 | 10 | 35 | 1 |
| 7b | 239 | 9.8 | 429 | 101 | 7340 | 892 | 41 | 474 | 1577 | 4 |
| 9a | 45 | 9.6 | 22 | 0 | 20 | 7 | 0 | 472 | 1531 | 3 |
| 9b | 45 | 9.6 | 22 | 0 | 20 | 7 | 0 | 472 | 1531 | 3 |
| 15a | 45 | 9.6 | 101 | 25 | 1824 | 221 | 10 | 1 | 12 | 0 |
| 15b | 45 | 9.6 | 101 | 25 | 1824 | 221 | 10 | 1 | 12 | 0 |

The highest temperature of the catalyst layer in Comparative Example 4 was 254° C. in the inner tubes 24a of the reactor 23a, and 254° C. in the inner tubes 24b of the reactor 23b. In this case, the temperature of the pressurized boiling water, a coolant, was 238° C. The carbon yield in Comparative Example 4 was 90.2%.

The difference between Example 15 and Comparative Example 4 is whether the circulation gas is allowed to flow serially in the respective reactors and the respective separators, or the unreacted gases separated from the respective separators are allowed to flow in the respective reactors in parallel with each other. In Example 15, there is one synthesis loop, and the reactors and the separators are serially arranged, and on the other hand, in Comparative Example 4, there are two synthesis loops, and the reactors and the separators are arranged in parallel with each other. The temperature of each of the separators was made equal to 45° C. both in Example 15 and Comparative Example 4. The carbon yield of Example 15 is higher by 6.5% than the carbon yield of Comparative Example 4, and thus the yield was improved in Example 15. In Comparative Example 4, as compared with Example 15, the number of the compressors for the circulation gas is increased, to result in poorer economic efficiency.

In particular, in Comparative Example 4, each of the synthesis loops has one separation step, hence the separation steps in the respective loops were operated under the same conditions, and accordingly in Table 24, under the heading of the second separation step, the temperature concerned and the methanol separation proportion are shown.

Comparative Example 5

In Comparative Example 5, the production apparatus shown in FIG. 5 was used. The involved conditions were as follows. Specifically, the molar flow rate of the raw material gas was set to be the same as in Example 15, and the synthesis of methanol was performed under the condition of the circulation ratio of 0.9.

In this case, the circulation ratio is defined by the molar flow rate of the circulation gas based on the molar flow rate of the make-up gas, and the molar flow rate of the circulation gas is the molar flow rate of the line 5.

The synthesis process in Comparative Example 5 is a combination of the reactor present in one synthesis loop and the reactor present in one single-pass reaction system.

The synthesis raw material gas including CO, $CO_2$ and $H_2$, produced by steam-reforming reaction was introduced into the system from the line 1, and was increased in pressure to a pressure of 9.9 MPa-G (101 kg/cm²-G) with the compressor 21. Then, 50 mol % of the synthesis raw material gas (make-up gas) increased in pressure was allowed to flow in the line 3, and supplied to the preheater 22. The make-up gas was subjected to the heat exchange in the preheater 22 with the outlet gas including the reaction product flowing in the line 7 from the reactor 23, thus preheated to 200° C., and supplied to the reactor 23 from the line 6. The residual make-up gas, namely, 50 mol % of the make-up gas was allowed to flow in a line 4a.

The reactor 23 had the inner tubes 24 made of a carbon steel, and the methanol synthesis catalyst C including copper and zinc as the essential components was filled in the inner tubes 24 to form the catalyst layer. Methanol was synthesized in the process allowing the make-up gas supplied from the line 6 into the reactor 23 to pass through the catalyst layer in the inner tubes 24. In the catalyst layer, the pressure of the fluid was 9.9 MPa-G (101 kg/cm²-G), and the temperature was between 200 and 260° C.

The outlet gas including methanol, flowing out from the reactor 23 into the line 7, was cooled in the preheater 22, then supplied to the condenser 25 and cooled to 45° C. to further condense methanol. Of the fluid including the condensed methanol, the condensed fraction was extracted as crude methanol from the line 9 to outside the system in the gas-liquid separator 26, and the vapor phase fraction was allowed to flow in the line 8.

necessary for the steam-reforming reaction in the production of the raw material gas from natural gas.

The mass balances are shown in Table 20. The line numbers in Table 20 are the line numbers shown in FIG. 5, and the temperature, the pressure and the material flow rates of the fluid flowing in each of the lines are shown.

TABLE 20

| Line number | Temperature ° C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 585 | 1113 | 5401 | 228 | 10 | 8 | 0 | 0 |
| 4a | 142 | 9.9 | 585 | 1113 | 5401 | 228 | 10 | 8 | 0 | 0 |
| 5 | 48 | 9.9 | 473 | 143 | 11075 | 1386 | 64 | 4 | 72 | 3 |
| 6 | 200 | 9.9 | 585 | 1113 | 5402 | 228 | 10 | 8 | 0 | 0 |
| 7 | 238 | 9.9 | 394 | 78 | 2759 | 228 | 10 | 202 | 1221 | 2 |
| 8 | 45 | 9.7 | 354 | 77 | 2745 | 224 | 10 | 1 | 18 | 1 |
| 9 | 45 | 9.7 | 40 | 1 | 15 | 4 | 0 | 201 | 1203 | 2 |
| 11 | 200 | 9.6 | 1411 | 1332 | 19221 | 1838 | 84 | 13 | 90 | 4 |
| 12 | 240 | 9.6 | 645 | 189 | 14635 | 1838 | 84 | 783 | 1992 | 8 |
| 14 | 45 | 9.4 | 21 | 1 | 24 | 9 | 0 | 778 | 1897 | 4 |
| 15 | 45 | 9.4 | 151 | 46 | 3536 | 443 | 20 | 1 | 23 | 1 |

The fraction of the make-up gas, allowed to flow in the line 4a, namely, 50 mol % of the make-up gas was mixed with the circulation gas from the line 5, and then further mixed with the unreacted gas from the line 8, the vapor phase fraction of the gas-liquid separator 26. The mixture was supplied to the preheater 27, subjected to the heat exchange in the preheater 27 with the outlet gas including the reaction product flowing in the line 12 of the outlet of the reactor 28, thus preheated to 200° C., and supplied to the reactor 28 from the line 11. The reactor 28 had the inner tubes 29 made of a carbon steel, and the methanol synthesis catalyst C including copper and zinc as the essential components was filled in the inner tubes 29 to form the catalyst layer. Methanol was synthesized in the process allowing the synthesis gas supplied from the line 11 into the reactor 28 to pass through the catalyst layer in the inner tubes 29.

The outlet gas including methanol, flowing out from the reactor 28 into the line 12, was cooled in the preheater 27, then supplied to the condenser 30 and cooled to 45° C. to further condense methanol. Of the fluid including the condensed methanol, the condensed fraction was extracted as crude methanol from the line 14 to outside the system in the gas-liquid separator 31, and the vapor phase fraction was allowed to flow in the line 13. Of the unreacted gas flowing in the line 13, the unreacted gas of an amount to give a predetermined circulation ratio was recycled as the circulation gas from the line 16 through the circulator 32 and then from the line 5 into the reactor 28, and the residual unreacted gas was extracted as the purge gas from the line 15 and from the synthesis loop to outside the system in order to remove the inert component accumulating in the synthesis loop.

The cooling operations of the catalyst layers in the reactors 23 and 28 were performed in the process in which the boiler water from the steam drum 33 was introduced from the lines 43 and 44 into the reactors 23 and 28, respectively, these boiler waters were used as the pressurized boiling waters, and the fluids including the produced steams were collected from the lines 44 and 46 respectively in the steam drum 33. The steam produced by the heat of reaction was taken out from the steam drum 33 to the line 42, and the amount of water to compensate the amount of the steam was supplied from the line 41 to the steam drum. The steam taken out from the line 42 can be used as the raw material steam The highest temperature of the catalyst layer in Comparative Example 5 was 260° C. in the inner tubes 24 of the reactor 23, and 251° C. in the inner tubes 29 of the reactor 28. In this case, the temperature of the pressurized boiling water, a coolant, was 238° C. The carbon yield in Comparative Example 5 was 91.3%.

The difference between Example 15 and Comparative Example 5 is whether the circulation gas is allowed to flow serially in the respective reactors and the respective separators, or the circulation gas is allowed to flow singly into the final reactor (reactor 28) and the first reactor (reactor 23) is allowed to present in the single-pass reaction system. In Example 15, there was one synthesis loop, and the reactors and the separators were serially arranged in the synthesis loop. On the other hand, in Comparative Example 5, the reactor 23 and the separator 26 not included in the synthesis loop were arranged, only the make-up gas was designed to be introduced into the reactor 23 and the unreacted gas from the separator 26 was designed to be introduced into the synthesis loop. The temperature of each of the separators was made equal to 45° C. both in Example 15 and Comparative Example 5. The carbon yield of Example 15 is higher by 5.4% than the carbon yield of Comparative Example 5, and thus the yield was improved in Example 15. Additionally, in Comparative Example 5, the flow rate of the mixture of the make-up gas and the unreacted gas, supplied to the reactor 28, was increased based on the flow rate of the make-up gas supplied to the reactor 23. Consequently, the load on the catalyst filled in the reactor 28 was higher than the load on the catalyst filled in the reactor 23, and thus, the loads on the respective catalyst layers were found to be uneven.

Example 16

In Example 16, the production apparatus shown in FIG. 6 was used. The involved conditions were as follows. Specifically, as the raw material gas, the gas produced by the steam-reforming reaction of natural gas was used, and the synthesis of methanol was performed under the condition of the circulation ratio of 0.9. As the catalysts in the reactors 23a, 23b and 23c, the methanol synthesis catalyst C was used. The raw material gas was increased in pressure to a pressure of 9.9 MPa-G (101 kg/cm$^2$-G) with the compressor 21. Then, 30 mol %, 30 mol % and 40 mol % of the synthesis raw material gas (make-up gas) increased in pressure were allowed to flow in the lines 3a, 3b and 3c, respectively. The mixed gas obtained by mixing the gas allowed to flow in the line 3a and the circulation gas from the line 5 was subjected to the heat exchange with the outlet gas (reaction mixture) including the reaction product, flowing in the line 7a of the outlet of the reactor 23a, and thus preheated to 200° C. As the reactor 23a, a reactor having the inner tubes 24a made of a carbon steel was used. In the catalyst layer, the pressure of the fluid was 9.8 MPa-G (100 kg/cm$^2$-G), and the temperature was between 200 and 261° C.

The outlet gas from the first synthesis step was cooled to a temperature equal to or lower than the dew point of methanol, namely, 80° C. (total pressure: 9.6 MPa-G (98 kg/cm$^2$-G)), to promote the condensation of methanol. The synthesis gas allowed to flow in the line 4b was subjected to the heat exchange in the preheater 22b with the outlet gas including the reaction product, flowing in the line 7b of the outlet of the reactor 23b, and thus preheated to 200° C. As the reactor 23b, a reactor having the inner tubes 24b made of a carbon steel was used. In the catalyst layer, the pressure of the fluid was 9.5 to 9.6 MPa-G (97 to 98 kg/cm$^2$-G), and the temperature was between 200 and 255° C. The outlet gas including methanol, flowing out from the reactor 23b into the line 7b, was cooled in the preheater 22b, and then cooled to 60° C. with the condenser 25b to further condense methanol.

The synthesis gas allowed to flow in the line 4c was subjected to the heat exchange in the preheater 22c with the outlet gas including the reaction product, flowing in the line 7c of the outlet of the reactor 23c, and thus preheated to 200° C. As the reactor 23c, a reactor having the inner tubes 24c made of a carbon steel was used. In the catalyst layer, the pressure of the fluid was 9.3 MPa-G (95 kg/cm$^2$-G), and the temperature was between 200 and 261° C. The outlet gas including methanol, flowing out from the reactor 23c into the line 7c, was cooled in the preheater 22c, and then cooled to 45° C. with the condenser 25c, to further condense methanol.

The mass balances are shown in Table 21. The line numbers in Table 21 are the line numbers shown in FIG. 6, and the temperature, the pressure and the material flow rates of the fluid flowing in each of the lines are shown.

The highest temperature of the catalyst layer in Example 16 was 261° C. in the inner tubes 24a of the reactor 23a, 255° C. in the inner tubes 24b of the reactor 23b and 261° C. in the inner tubes 24c of the reactor 23c, these temperatures falling within an extremely preferable temperature range as the catalyst use temperature range. In this case, the temperature of the pressurized boiling water, a coolant, was 230° C.

The carbon yield in Example 16 is represented by the methanol molar flow rate (the sum of the methanol molar flow rates in the line 9a, the line 9b and the line 9c) in the crude methanol based on the sum of the CO molar flow rate and the CO$_2$ molar flow rate in the make-up gas (the sum of the CO molar flow rates and the CO$_2$ molar flow rates in the line 3a, the line 3b and the line 3c), and was 97.5%.

Example 17

In Example 17, the production apparatus shown in FIG. 1 was used. The involved conditions were as follows. Specifically, the raw material gas was regulated to have the same composition as the composition of the raw material gas used in Example 1, and the synthesis of methanol was performed under the condition of the circulation ratio of 1.2.

Additionally, 40 mol % of the make-up gas was allowed to flow in the line 3, and the residual make-up gas, namely, 60 mol % of the make-up gas was allowed to flow in the line 4. The outlet gas from the first synthesis step was cooled to 80° C. with the condenser 25 to promote the condensation of methanol. The amount of the purge gas extracted from the line 15 to outside the system was regulated so as for the circulation ratio to be 1.2. The pressure increased with the compressor 21 and the temperatures in the line 6 and the line 11 were also set to be the same as in Example 1. A carbon steel was used for the materials of the inner tubes 24 of the reactor 23 and the inner tubes 29 of the reactor 28, and the methanol synthesis catalyst D was filled in the reactor 23 and the reactor 28.

The mass balances are shown in Table 22. The line numbers in Table 22 are the line numbers shown in FIG. 1, and the temperature, the pressure and the material flow rates of the fluid flowing in each of the lines are shown.

TABLE 21

| Line number | Temperature ° C. | Pressure MPa-G | Flow rate kg-mol/h | | | | | | | |
|---|---|---|---|---|---|---|---|---|---|---|
| | | | CO$_2$ | CO | H$_2$ | CH$_4$ | N$_2$ | H$_2$O | CH$_3$OH | Impurity |
| 3a | 142 | 9.9 | 348 | 662 | 3215 | 136 | 6 | 5 | 0 | 0 |
| 3b | 142 | 9.9 | 348 | 662 | 3215 | 136 | 6 | 5 | 0 | 0 |
| 3c | 142 | 9.9 | 464 | 883 | 4286 | 181 | 8 | 6 | 0 | 0 |
| 5 | 54 | 9.9 | 128 | 38 | 11123 | 1668 | 77 | 4 | 73 | 4 |
| 6a | 200 | 9.8 | 476 | 700 | 14337 | 1804 | 83 | 8 | 73 | 4 |
| 7a | 230 | 9.8 | 101 | 28 | 11870 | 1804 | 83 | 385 | 1115 | 6 |
| 8a | 80 | 9.6 | 100 | 28 | 11858 | 1802 | 83 | 22 | 301 | 5 |
| 9a | 80 | 9.6 | 1 | 0 | 13 | 2 | 0 | 363 | 815 | 1 |
| 6b | 200 | 9.6 | 448 | 690 | 15072 | 1938 | 89 | 27 | 301 | 5 |
| 7b | 231 | 9.6 | 112 | 35 | 12753 | 1937 | 89 | 366 | 1288 | 7 |
| 8b | 60 | 9.4 | 110 | 35 | 12738 | 1933 | 89 | 8 | 154 | 5 |
| 9b | 60 | 9.4 | 2 | 0 | 16 | 5 | 0 | 357 | 1134 | 2 |
| 6c | 200 | 9.3 | 574 | 918 | 17024 | 2113 | 97 | 15 | 154 | 5 |
| 7c | 231 | 9.3 | 165 | 48 | 16615 | 2113 | 97 | 426 | 1428 | 7 |
| 9c | 45 | 9.1 | 4 | 0 | 17 | 7 | 0 | 421 | 1336 | 3 |
| 15 | 45 | 9.1 | 34 | 10 | 5476 | 438 | 20 | 1 | 19 | 1 |

TABLE 22

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 142 | 9.9 | 476 | 906 | 4399 | 186 | 8 | 7 | 0 | 0 |
| 4 | 142 | 9.9 | 714 | 1360 | 6599 | 278 | 13 | 10 | 0 | 0 |
| 5 | 51 | 9.9 | 372 | 193 | 15073 | 2106 | 97 | 4 | 98 | 5 |
| 6 | 200 | 9.9 | 849 | 1099 | 19473 | 2291 | 105 | 11 | 98 | 5 |
| 7 | 248 | 9.8 | 294 | 120 | 15853 | 2291 | 105 | 568 | 1624 | 8 |
| 8 | 80 | 9.6 | 291 | 120 | 15835 | 2289 | 105 | 30 | 403 | 6 |
| 9 | 80 | 9.6 | 3 | 0 | 19 | 2 | 0 | 538 | 1222 | 2 |
| 11 | 200 | 9.6 | 1005 | 1480 | 22434 | 2567 | 117 | 40 | 403 | 6 |
| 12 | 249 | 9.6 | 465 | 234 | 18323 | 2567 | 117 | 583 | 2181 | 10 |
| 14 | 45 | 9.4 | 13 | 1 | 26 | 11 | 0 | 578 | 2063 | 4 |
| 15 | 45 | 9.4 | 80 | 41 | 3224 | 450 | 21 | 1 | 21 | 1 |

In Example 17, the temperature of the pressurized boiling water, a coolant, was 247° C. In this case, the highest temperature of the catalyst layer was 268° C. in the inner tubes 24 of the reactor 23, and 267° C. in the inner tubes 29 of the reactor 28, and the carbon yield was 95.0%.

Comparative Example 6

In Comparative Example 6, the production apparatus shown in FIG. 7 was used. Comparative Example 6 is different from Example 13 in the position of the circulator. The composition and the total molar flow rate of the raw material gas were set to be the same as in Example 13, and the discharge pressure of the circulator 32 were also set to be the same as in Example 13. A stainless steel was used for the materials of the inner tubes 24 of the reactor 23 and the inner tubes 29 of the reactor 28, and the methanol synthesis catalyst C was filled in the reactor 23 and the reactor 28. Comparative Example 6 is based on the technique of Patent Document 3.

The mass balances are shown in Table 23. The line numbers in Table 23 are the line numbers shown in FIG. 7, and the temperature, the pressure and the material flow rates of the fluid flowing in each of the lines are shown.

TABLE 23

| Line number | Temperature °C. | Pressure MPa-G | Flow rate kg-mol/h | | | | | | | |
|---|---|---|---|---|---|---|---|---|---|---|
| | | | $CO_2$ | CO | $H_2$ | $CH_4$ | $N_2$ | $H_2O$ | $CH_3OH$ | Impurity |
| 3 | 139 | 9.6 | 578 | 1101 | 5343 | 225 | 10 | 8 | 0 | 0 |
| 4 | 139 | 9.6 | 578 | 1101 | 5343 | 225 | 10 | 8 | o | 0 |
| 6 | 200 | 9.6 | 738 | 1138 | 22660 | 2819 | 130 | 14 | 108 | 5 |
| 7 | 226 | 9.6 | 191 | 44 | 18831 | 2819 | 130 | 564 | 1742 | 8 |
| 8 | 50 | 9.4 | 187 | 44 | 18811 | 2811 | 130 | 8 | 150 | 5 |
| 9 | 50 | 9.4 | 4 | 0 | 21 | 8 | 0 | 556 | 1592 | 3 |
| 10b | 82 | 9.9 | 765 | 1145 | 24154 | 3036 | 140 | 16 | 150 | 5 |
| 11 | 200 | 9.9 | 765 | 1145 | 24154 | 3036 | 140 | 16 | 150 | 5 |
| 12 | 226 | 9.8 | 191 | 43 | 20226 | 3036 | 140 | 594 | 1820 | 9 |
| 14 | 45 | 9.6 | 4 | 0 | 22 | 10 | 0 | 588 | 1694 | 3 |
| 15 | 45 | 9.6 | 27 | 6 | 2887 | 432 | 20 | 1 | 18 | 1 |
| 16 | 45 | 9.6 | 160 | 37 | 17316 | 2594 | 120 | 6 | 108 | 5 |

More specifically, in Example 13, the pressure of the circulation gas in the line 16, which was the residual unreacted gas obtained by removing the purge gas discharged through the line 15 from the unreacted gas discharged from the second gas-liquid separator 31 through the line 13, was increased through the circulator 32. On the contrary, in Comparative Example 6, the pressure of the gas flowing in the line 10a, which was the mixture of the unreacted gas discharged from the first gas-liquid separator 26 through the line 8 and a fraction of the make-up gas flowing in the line 4, was increased through the circulator 32. Such difference causes the difference in the inlet pressure of each of the reactor 23 and the reactor 28 between the example and the comparative example.

The composition and the total molar flow rate of the raw material gas were set to be the same as in Example 13, and the discharge pressure of the circulator 32 were also set to The highest temperature of the catalyst layer in Comparative Example 6 was 263° C. in the inner tubes 24 of the reactor 23, and 262° C. in the inner tubes 29 of the reactor 28. In this case, the temperature of the pressurized boiling water, a coolant, was 225° C. The carbon yield in Comparative Example 6 was 97.9%.

The difference between Example 13 and Comparative Example 6 is the position of the circulator, and this difference results in the difference in the pressure of each of the reactors. The amount of the gas throughput at the circulator in Example 13 was 20347 kg-mol/h, whereas the amount in Comparative Example 6 was 29411 kg-mol/h. It is not preferable in Comparative Example 6 since the load of the circulator is higher than that in Example 13.

The results of foregoing Examples and Comparative Examples are collected in Tables 24 to 26.

TABLE 24

| | Make-up gas division proportions (mol %) | | | Circulation ratio | Highest temperature of catalyst layer in first synthesis step (° C.) | Highest temperature of catalyst layer in second synthesis step (° C.) | Highest temperature of catalyst layer in third synthesis step (° C.) |
|---|---|---|---|---|---|---|---|
| | For first mixed gas | For second mixed gas | For third mixed gas | | | | |
| Example 1 | 40% | 60% | — | 1.0 | 262 | 267 | — |
| Comparative Example 1 | 40% | 60% | — | 1.0 | 243 | 238 | — |
| Comparative Example 2 | 40% | 60% | — | 3.0 | 248 | 241 | — |
| Example 2 | 50% | 50% | — | 1.1 | 261 | 259 | — |
| Comparative Example 3 | 100% | 0% | — | 1.1 | 269 | 238 | — |
| Example 3 | 40% | 60% | — | 0.8 | 262 | 261 | — |
| Example 4 | 50% | 50% | — | 0.6 | 260 | 259 | — |
| Example 5 | 70% | 30% | — | 1.6 | 263 | 252 | — |
| Example 6 | 40% | 60% | — | 1.2 | 267 | 266 | — |
| Example 7 | 40% | 60% | — | 1.0 | 261 | 261 | — |
| Example 8 | 60% | 40% | — | 1.0 | 264 | 265 | — |
| Example 9 | 30% | 70% | — | 1.5 | 265 | 266 | — |
| Example 10 | 40% | 60% | — | 1.7 | 267 | 267 | — |
| Example 11 | 40% | 60% | — | 1.2 | 267 | 266 | — |
| Example 12 | 24% | 76% | — | 1.2 | 261 | 270 | — |
| Example 13 | 50% | 50% | — | 1.4 | 265 | 261 | — |
| Example 14 | 50% | 50% | — | 1.4 | 237 | 235 | — |
| Example 15 | 50% | 50% | — | 0.9 | 267 | 264 | — |
| Comparative Example 4 | 50% | 50% | — | 0.9 | 254 | 254 | — |
| Comparative Example 5 | 50% | 50% | — | 0.9 | 260 | 251 | — |
| Example 16 | 30% | 30% | 40% | 0.9 | 261 | 255 | 261 |
| Example 17 | 40% | 60% | — | 1.2 | 268 | 266 | — |
| Comparative Example 6 | 50% | 50% | — | 1.4 | 263 | 262 | — |

TABLE 25

| | First separation step | | Second separation step | | Third separation step | |
|---|---|---|---|---|---|---|
| | Temperature (° C.) | Methanol division proportion | Temperature (° C.) | Methanol division proportion | Temperature (° C.) | Methanol division proportion |
| Example 1 | 45 | 94.4% | 45 | 95.0% | — | — |
| Comparative Example 1 | — | — | 45 | 96.4% | — | — |
| Comparative Example 2 | — | — | 45 | 92.7% | — | — |
| Example 2 | 45 | 94.5% | 45 | 93.9% | — | — |
| Comparative Example 3 | 45 | 95.8% | 45 | 85.7% | — | — |
| Example 3 | 80 | 81.5% | 45 | 96.0% | — | — |
| Example 4 | 30 | 98.3% | 45 | 95.9% | — | — |
| Example 5 | 20 | 98.2% | 45 | 88.2% | — | — |
| Example 6 | 80 | 74.2% | 45 | 94.9% | — | — |
| Example 7 | 80 | 77.9% | 45 | 95.5% | — | — |
| Example 8 | 60 | 91.0% | 45 | 93.9% | — | — |
| Example 9 | 100 | 35.8% | 45 | 95.1% | — | — |
| Example 10 | 70 | 77.1% | 45 | 92.7% | — | — |
| Example 11 | 80 | 75.6% | 45 | 94.3% | — | — |
| Example 12 | 80 | 68.1% | 45 | 95.5% | — | — |
| Example 13 | 50 | 91.7% | 45 | 92.8% | — | — |
| Example 14 | 50 | 91.5% | 45 | 92.5% | — | — |
| Example 15 | 45 | 95.3% | 45 | 94.8% | — | — |
| Comparative Example 4 | — | — | 45 | 97.0% | — | — |
| Comparative Example 5 | 45 | 98.5% | 45 | 95.3% | — | — |
| Example 16 | 80 | 73.1% | 60 | 88.0% | 45 | 93.5% |
| Example 17 | 80 | 75.2% | 45 | 94.6% | — | — |
| Comparative Example 6 | 50 | 91.4% | 45 | 93.1% | — | — |

TABLE 26

| | Carbon yield | Methanol synthesis catalyst | Ratio between methanol production amounts of respective reactors (maximum/minimum) | Amount of gas throughput at circulator (kg-mol/h) |
|---|---|---|---|---|
| Example 1 | 96.9% | Catalyst C | 1.3 | 14661 |
| Comparative Example 1 | 83.5% | Catalyst C | 1.5 | 14713 |
| Comparative Example 2 | 96.9% | Catalyst C | 1.2 | 44135 |
| Example 2 | 97.3% | Catalyst C | 1.0 | 16073 |
| Comparative Example 3 | 97.9% | Catalyst C | 4.3 | 16073 |
| Example 3 | 95.2% | Catalyst C | 1.3 | 11937 |
| Example 4 | 94.5% | Catalyst C | 1.0 | 9023 |
| Example 5 | 98.3% | Catalyst C | 1.8 | 23139 |
| Example 6 | 96.9% | Catalyst C | 1.3 | 17598 |
| Example 7 | 96.6% | Catalyst C | 1.3 | 14712 |
| Example 8 | 96.9% | Catalyst B | 1.3 | 14673 |
| Example 9 | 96.0% | Catalyst B | 1.5 | 22221 |
| Example 10 | 96.1% | Catalyst A | 1.1 | 25144 |
| Example 11 | 93.4% | Catalyst A | 1.1 | 18255 |
| Example 12 | 96.1% | Catalyst C | 2.1 | 17738 |
| Example 13 | 97.8% | Catalyst C | 1.0 | 20347 |
| Example 14 | 95.3% | Catalyst C | 1.0 | 20885 |
| Example 15 | 96.7% | Catalyst C | 1.0 | 13220 |
| Comparative Example 4 | 90.2% | Catalyst C | 1.0 | 13220 |
| Comparative Example 5 | 91.3% | Catalyst C | 2.6 | 13220 |
| Example 16 | 97.5% | Catalyst C | 1.3 | 13115 |
| Example 17 | 95.0% | Catalyst D | 1.2 | 17948 |
| Comparative Example 6 | 97.8% | Catalyst C | 1.0 | 29411 |

The present application is based on Japanese Patent Application (Japanese Patent Application No. 2014-214081) filed on Oct. 20, 2014, and the contents thereof are incorporated herein by reference.

According to the method of the present invention, the catalyst layer temperature is appropriately maintained while the circulation ratio is being reduced, at the same time, the carbon yield in the methanol synthesis can be enhanced, moreover the unevenness of the loads on the respective catalyst layers can be reduced, and the reaction can be allowed to proceed more efficiently. Accordingly, the present invention has industrial applicability in the method for producing methanol and the apparatus for producing methanol.

REFERENCE SIGNS LIST

21: compressor; 32, 32a, 32b: circulator; 22, 22a, 22b, 22c, 27: preheater; 23, 23a, 23b, 23c, 28: reactor; 24, 24a, 24b, 24c, 29: inner tubes; 25, 25a, 25b, 25c, 30: condenser; 26, 26a, 26b, 26c, 31: gas-liquid separator; 33, 33a, 33b, 33c, 34: steam drum

The invention claimed is:

1. A method for producing methanol comprising: synthesis steps of synthesizing methanol from a synthesis gas comprising hydrogen, carbon monoxide and carbon dioxide; and separation steps of separating an unreacted gas from a reaction mixture obtained by passing through one of the synthesis steps, the method comprising a synthesis loop having at least two of the synthesis steps and at least two of the separation steps, wherein the synthesis loop comprises: a first mixing step of obtaining a first mixed gas by increasing through a circulator a pressure of a residual gas, obtained by removing a purge gas from a final unreacted gas separated from a final reaction mixture in a final separation step subsequent to a final synthesis step, and by mixing the residual gas with 10 to 90 mol % of a make-up gas comprising hydrogen, carbon monoxide and carbon dioxide; a first synthesis step of synthesizing methanol from the first mixed gas; a first separation step of separating a first unreacted gas from a first reaction mixture obtained in the first synthesis step; a second mixing step of obtaining a second mixed gas by mixing the first unreacted gas and at least a fraction of 10 to 90 mol % of the make-up gas; the final synthesis step of finally synthesizing methanol; and the final separation step of separating the final unreacted gas from the final reaction mixture obtained in the final synthesis step, and at least in the final synthesis step, a reaction temperature of a catalyst layer is controlled by indirect heat exchange with pressurized boiling water.

2. The method for producing methanol according to claim 1, wherein at least one separation step of the at least two separation steps comprised in the synthesis loop is a step of separating with a gas-liquid separator a liquid comprising methanol, produced by cooling the gaseous reaction mixture.

3. The method for producing methanol according to claim 1, wherein the first unreacted gas is mixed with 40 to 70 mol % of the make-up gas.

4. The method for producing methanol according to claim 1, wherein in the first separation step, the first unreacted gas is obtained by separating 35 to 100 mol % of the methanol in the first reaction mixture.

5. The method for producing methanol according to claim 1, wherein in the first separation step, the first unreacted gas is obtained by separating 75 to 96 mol % of the methanol in the first reaction mixture.

6. The method for producing methanol according to claim 1, wherein a circulation ratio, which is a ratio of a molar flow rate of the residual gas obtained by removing the purge gas from the final unreacted gas to a molar flow rate of the make-up gas, is within a range from 0.6 to 2.0.

7. The method for producing methanol according to claim 6, wherein the circulation ratio is within a range from 0.8 to 1.5.

8. The method for producing methanol according to claim 1, wherein a temperature of the pressurized boiling water is within a range from 220° C. to 260° C.

9. The method for producing methanol according to claim 1, wherein the final synthesis step is a step of synthesizing methanol from the second mixed gas, or a step of synthesizing methanol from a second unreacted gas or a third mixed gas obtained by mixing the second unreacted gas and a fraction of the make-up gas, the second unreacted gas being separated from a second reaction mixture obtained in the step of synthesizing methanol from the second mixed gas.

10. The method for producing methanol according to claim 1, wherein the final synthesis step is a step of synthesizing methanol from the second mixed gas.

11. The method for producing methanol according to claim 1, wherein a catalyst used in each of the synthesis steps comprises copper atoms and zinc atoms in an atomic ratio (copper/zinc) of 2.0 to 3.0, and further comprises aluminum atoms.

12. The method for producing methanol according to claim 1, wherein a catalyst used in each of the synthesis steps comprises copper atoms and zinc atoms in an atomic ratio (copper/zinc) of 2.1 to 3.0, and further comprises alumina in a content of 3% to 20% by mass, and is prepared by a production method comprising: a step of producing a precipitate comprising copper and zinc by mixing an aqueous solution comprising copper, an aqueous solution comprising zinc and an alkali aqueous solution; a step of obtaining a mixture by mixing the precipitate and an alumina hydrate having a pseudo boehmite structure; and a step of molding the mixture so as for the density to be 2.0 to 3.0 g/mL.

13. The method for producing methanol according to claim 1, wherein the proportion of the make-up gas to be mixed with the first unreacted gas is controlled according to a temperature of a reactor in the synthesis step.

14. The method for producing methanol according to claim 1, wherein in each of all of the synthesis steps, a reaction temperature of a catalyst layer is controlled by indirect heat exchange with pressurized boiling water.

* * * * *